US008303945B2

(12) United States Patent
Dahlén et al.

(10) Patent No.: US 8,303,945 B2
(45) Date of Patent: Nov. 6, 2012

(54) MUTANTS OF INTERLEUKIN-1 RECEPTOR ANTAGONIST

(75) Inventors: Eva Maria Dahlén, Arlöv (SE); Karin Elisabeth Barchan, Kalgshamn (SE); Patrick Thomas Höjman, Malmö (SE); Cecilia Ann-Christin Malmborg Hager, Helsingborg (SE); Marie Asa Ingegerd Karlsson, Lund (SE); Mats Peter Anderson, Kävlinge (SE); Björn Ulrik Walse, Lund (SE)

(73) Assignee: Alligator Bioscience AB, Lund (SE)

( * ) Notice: Subject to any disclaimer, the term of this patent is extended or adjusted under 35 U.S.C. 154(b) by 0 days.

(21) Appl. No.: 12/598,140

(22) PCT Filed: May 1, 2008

(86) PCT No.: PCT/GB2008/001510
§ 371 (c)(1),
(2), (4) Date: Dec. 7, 2009

(87) PCT Pub. No.: WO2008/132485
PCT Pub. Date: Nov. 6, 2008

(65) Prior Publication Data
US 2010/0120684 A1    May 13, 2010

(30) Foreign Application Priority Data
May 1, 2007    (GB) .................... 0708376.9

(51) Int. Cl.
*C07K 14/715*    (2006.01)
*A61K 38/19*    (2006.01)
(52) U.S. Cl. .................... 424/85.2; 530/351; 530/402
(58) Field of Classification Search .................... None
See application file for complete search history.

(56) References Cited

U.S. PATENT DOCUMENTS

| | | | |
|---|---|---|---|
| 5,643,872 A | 7/1997 | Ali et al. | |
| 5,831,012 A | 11/1998 | Nilsson et al. | |
| 5,922,573 A | 7/1999 | Boraschi et al. | |
| 6,008,058 A | 12/1999 | Spatola et al. | |
| 6,096,728 A | 8/2000 | Collins et al. | |
| 6,159,460 A | 12/2000 | Thompson et al. | |
| 6,294,170 B1 | 9/2001 | Boone et al. | |
| 6,599,873 B1 | 7/2003 | Sommer et al. | |

FOREIGN PATENT DOCUMENTS

| | | |
|---|---|---|
| EP | 0 343 684 A1 | 11/1989 |
| EP | 0 343 684 B1 | 11/1989 |
| EP | 0 367 576 A2 | 5/1990 |
| EP | 0 367 576 A3 | 5/1990 |
| EP | 0 422 339 A1 | 4/1991 |
| EP | 0 422 339 B1 | 4/1991 |
| EP | 0 480 950 B1 | 4/1992 |
| EP | 0 485 392 B1 | 5/1992 |
| EP | 0 541 920 A1 | 5/1993 |
| EP | 0 541 920 B1 | 5/1993 |
| EP | 0 575 545 B1 | 12/1993 |
| EP | 0 595 796 B1 | 5/1994 |
| EP | 0 615 448 B1 | 9/1994 |
| EP | 0 790 306 A2 | 8/1997 |
| EP | 0 790 306 A3 | 8/1997 |
| EP | 0 811 006 B1 | 12/1997 |
| EP | 0 857 487 A2 | 8/1998 |
| EP | 0 857 487 A3 | 8/1998 |
| EP | 0 904 112 B1 | 3/1999 |
| EP | 0 943 328 A2 | 9/1999 |
| EP | 0 943 328 A3 | 9/1999 |
| EP | 0 943 328 B1 | 9/1999 |
| EP | 1 133 995 A2 | 9/2001 |
| EP | 1 133 995 A3 | 9/2001 |
| WO | WO 9117184 | * 11/1991 |
| WO | WO 9510298 | * 1/1995 |
| WO | WO-95/34326 A1 | 12/1995 |
| WO | WO-96/09323 A1 | 3/1996 |
| WO | WO-00/21437 A2 | 4/2000 |
| WO | WO/00/21437 A3 | 4/2000 |
| WO | WO-02/48351 A2 | 6/2002 |
| WO | WO-02/48351 A3 | 6/2002 |
| WO | WO-02/062375 A1 | 8/2002 |
| WO | WO-03/059973 A2 | 7/2003 |
| WO | WO-03/059973 A3 | 7/2003 |
| WO | WO-03/097834 A2 | 11/2003 |
| WO | WO-03/097834 A3 | 11/2003 |
| WO | WO-2005/007197 A2 | 1/2005 |
| WO | WO-2005/007197 A3 | 1/2005 |
| WO | WO-2007/057682 A1 | 5/2007 |
| WO | WO-2008/132485 A2 | 11/2008 |
| WO | WO-2008/132485 A3 | 11/2008 |

OTHER PUBLICATIONS

Mikayama et al. Proc. Natl. Acad. Sci. USA (1993) vol. 90, pp. 10056-10060.*

(Continued)

*Primary Examiner* — Prema Mertz
(74) *Attorney, Agent, or Firm* — Morrison & Foerster LLP

(57) ABSTRACT

The invention provides an isolated polypeptide comprising a variant amino acid sequence of SEQ ID NO: 1, or a fusion or derivative of said polypeptide, or a fusion of a said derivative thereof, wherein the polypeptide, fusion or derivative retains a biological activity of wild type IL-IRa. In one embodiment, the isolated polypeptide, fusion or derivative is or comprises a polypeptide variant of amino acid sequence SEQ ID NO: 1 comprising or consisting of substitutions at one or more of the following amino acid mutations of SEQ ID NO: 1: Q29K, P38Y, P38R, L42W, D47N, E52R, H54R, E90Y, Q129L, Q129N, M136N, M136D and Q149K. Also provided are pharmaceutical compositions of the above polypeptide, fusion or derivative, as well as uses of the same for treating a disease or condition capable of being treated by an agent which inhibits the function of IL-1 receptors.

7 Claims, 5 Drawing Sheets

OTHER PUBLICATIONS

Voet et al. Biochemistry John Wiley & Sons, Inc., (1990) pp. 126-128 and 228-234.*
Abuchowski, A. et al. (Jun. 10, 1977). "Alteration of Immunological Properties of Bovine Serum Albumin by Covalent Attachment of Polyethylene Glycol," *The Journal of Biological Chemistry* 252(11):3578-3581.
Arend, P.W. et al. (May 19, 2000). "Physiologic Role of Interleukin-1 Receptor Antagonist," *Arthritis Res.* 2(4):245-248.
Ausubel, F.M. et al. (1999). "DNA Sequencing," Chapter 7 *in Current Protocols in Molecular Biology*, Supplement 47, pp. 7.0.1-7.0.15.
Baudyš, M. et al. (1998, e-pub. Feb. 5, 1998). "Extending Insulin Action in Vivo by Conjugation to Carboxymethyl Dextran," *Bioconjugate Chem.* 9:176-183.
Becker, D.M. et al. (1991). "High-Efficiency Transformation of Yeast by Electroporation," *Methods in Enzymology* 194:182-187.
Behe, M. et al. (2001). "Biodistribution, Blood Half-Life, and Receptor Binding of a Somatostatin-Dextran Conjugate," *Medical Oncology* 18(1):59-64.
Bodar, E.J. (Jul.-Aug. 2005). "Effect of Entanercept and Anakinra on Inflammatory Attacks in the Hyper-IgD Syndrome: Introducing a Vaccination Provocation Model," *The Journal of Medicine* 63(7):260-264.
Boschan, C. et al. (2006). "Neonatal-Onset Multisystem Inflammatory Disease (NOMID) Due to a Novel S331R Mutation of the *CIAS1* Gene and Response to the Interleukin-1 Receptor Antagonist Treatment," *American Journal of Medical Genetics* 140A:883-886.
Bowen, S. et al. (1999). "Relationship Between Molecular Mass and Duration of Activity of Polyethylene Glycol Conjugated Granulocyte Colony-Stimulating Factor Mutein," *Experimental Hematology* 27:425-432.
Bresnihan, B. et al. (Dec. 1998). "Treatment of Rheumatoid Arthritis with Recombinant Human Interleukin-1 Receptor Antagonist," *Arthritis & Rheumatism* 41(12):2196-2204.
Burger, D. et al. (2006). "Is IL-1 a Good Therapeutic Target in the Treatment of Arthritis?" *Best Practices and Research Clinical Rheumatology* 20(5):879-896.
Chae, J.J. et al. (Jun. 27, 2006). "The B30.2 Domain of Pyrin, the Familial Mediterranean Fever Protein, Interacts Directly with Caspase-1 to Modulate Il-1 β Production," *PNAS* 103(26):9982-9987.
Chan, W-L. et al. (1999). "Lowering of Trichosanthin Immunogenicity by Site-Specific Coupling to Dextran," *Biochemical Pharmacology* 57:927-934.
Chapman, A.P. et al. (Aug. 1999). "Therapeutic Antibody Fragments with Prolonged in vivo Half-Lives," *Nature Biotechnology* 17:780-1783.
Chapman, A.P. (2002). "PEGylated Antibodies and Antibody Fragments for Improved Therapy: A Review," *Advanced Drug Delivery Reviews* 54:531-545.
Chevalier, X. et al. (2005). "Safety Study of Intraarticular Injection of Interleukin 1 Receptor Antagonist in Patients with Painful Knee Osteoarthritis: A Multicenter Study," *The Journal of Rheumatology* 32(7):1317-1323.
Cohen, S. et al. (Mar. 2002). "Treatment of Rheumatoid Arthritis With Anakinra, a Recombinant Human Interleukin-1 Receptor Antagonist, in Combination With Methotrexate," *Arthritis & Rheumatism* 46(3):614-624.
Cohen, S.B. et al. (2004, e-pub. Apr. 13, 2004). "A Multicentre, Double Blind, Randomised, Placebo Controlled Trial of Anakinra (Kineret), a Recombinant Interleukin 1 Receptor Antagonist, in Patients with Rheumatoid Arthritis Treated with Background Methotrexate," *Ann. Rheum. Dis.* 63:1062-1068.
Dahlén, E. et al. (2008). "Development of Interleukin-1 Receptor Antagonist Mutants with Enhanced Antagonistic Activity In Vitro and Improved Therapeutic Efficacy in Collagen-Induced Arthritis," *Journal of Immunotoxicology* 5:189-199.
Delgado, C. et al. (1996). "Enhanced Tumour Specificity of an Anti-Carcinoembrionic Antigen Fab' Fragment by Poly(Ethylene Glycol) (PEG) Modification," *British Journal of Cancer* 73:175-182.
Dierselhius, M.P. et al. (2005, e-pub. Jan. 5, 2005). "Anakinra for Flares of Pyogenic Arthritis in PAPA Syndrome," *Rheumatology* 44(3):406-408.
Dinarello, C.A. (Mar. 15, 1996). "Biological Basis for Interleukin-1 in Disease," *Blood* 87(6):2095-2147.
Dinarello, C.A. (Aug. 2000). "Impact of Basic Research on Tomorrow's Medicine. Proinflammatory Cytokines," *Chest* 118(2):503-508.
Dinarello, C.A. (2002). "The IL-1 Family and Inflammatory Diseases," *Clin. Exp. Rheumatol.* 20(Suppl. 27):S1-S13.
Doyle, P.M. et al. (1996). "Solution Structure of a Biologically Active Cyclic LDV Peptide Analogue Containing a Type II' β-Turn Mimetic," *Int. J. Peptide Protein Res.* 47:427-436.
Elliot, S. et al. (Apr. 2003, e-pub. Mar. 3, 2002). "Enhancement of Therapeutic Protein in vivo Activates Through Glycoengineering," *Nature Biotechnology* 21:414-421.
Evans, R.J. et al. (May 12, 1995). "Mapping Receptor Binding Sites in Interleukin (IL)-1 Receptor Antagonist and IL-1β by Site-Directed Mutagenesis," *The Journal of Biological Chemistry* 270(19):11477-11483.
Examination Report mailed on Mar. 26, 2004, for EP Patent Application No. 02710840.6, 5 pages.
Fields, G.B. ed. (1997). *Methods in Enzymology: Solid-Phase Peptide Synthesis*, Academic Press: New York, NY, vol. 289, pp. v-vii, (Table of Contents Only.).
Fitzgerald, A.A. et al. (Jun. 2005). "Rapid Responses to Anakinra in Patients With Refractory Adult-Onset Still's Disease," *Arthritis & Rheumatism* 52(6):1794-1803.
Francis, G.E. et al. (1992). "PEG-Modified Proteins," Chapter 8 *in Stability of Protein Pharmaceuticals Part B: In Vivo Pathways of Degradation and Strategies for Protein Stabilization*, Ahern, T.J. et al. eds., Plenum Press: New York, NY, pp. 235-263.
Gietz, R.D. et al. (Apr. 2001). "Genetic Transformation of Yeast," *BioTechniques* 30(4):816-831.
Gennaro, A.R. ed. (1995). *Remington: The Science and Practice of Pharmacy*, 19th Edition, Mack Publishing Company: Easton, PN, pp. xv-xvi, (Table of Contents Only.).
Goldenberg, M.M. (1999). "Enanercept, A Novel Drug for the Treatment of Patients with Severe, Active Rheumatoid Arthritis," *Clinical Therapeutics* 21(1):75-87.
Goodson, R.J. et al. (Apr. 1990). "Site-Directed Pegylation of Recombinant Interleukin-2 at its Glycosylation Site," *Bio/Technology* 8:343-346.
Greenwald, R.B. et al. (2000). "Poly(Ethylene Glycol) Conjugated Drugs and Prodrugs: A Comprehensive Review," *Critical Reviews in Therapeutic Drug Carrier Systems* 17(2):101-161.
Hamilton-Wessler, M. et al. (1999). "Mechanism of Protracted Metabolic Effects of Fatty Acid, Acylated Insulin, NN304, in Dogs: Retention of NN304 by Albumin," *Diabetologia* 42:1254-1263.
Hawkins, P.N. et al. (Jun. 19, 2003). "Interleukin-1-Receptor Antagonist in the Muckle-Wells Syndrome," *N. Engl. J. Med.* 348(25):2583-2584.
Hawkins, P.N. et al. (Feb. 2004). "Spectrum of Clinical Features in Muckle-Wells Syndrome and Response to Anakinra," *Arthritis & Rheumatism* 50(2):607-612.
Herman, S. et al. (1994). "End-group Modification of a α-Hydro-ω-Methoxy-Poly(Oxyethylene), 3[a]," *Macromol. Chem. Phys.* 195:203-209.
Hershfield, M.S. et al. (Aug. 1991). "Use of Site-Directed Mutagenesis to Enhance the Epitope-Shielding Effect of Covalent Modification of Proteins with Polyethylene Glycol," *PNAS* 88:7185-7189.
Hoffman, H.M. et al. (Nov. 13, 2004). "Prevention of Cold-Associated Acute Inflammation in Familial Cold Autoinflammatory Syndrome by Interleukin-1 Receptor Antagonist," *The Lancet* 364:1779-1785.
International Search Report mailed on Jan. 16, 2009, for PCT Patent Application No. PCT/GB2008/001510, filed on May 1, 2008, 8 pages.
Kim, D.S. (2001). "Synthesis and Properties of Dextran-Linked Ampicillin," *Drug Development and Industrial Pharmacy* 27(1):97-101.
Kitamura, K. et al. (Aug. 15, 1991). "Chemical Engineering of the Monoclonal Antibody A7 by Polyethylene Glycol for Targeting Cancer Chemotherapy," *Cancer Research* 51:4310-4315.
Kurtzhals, P. et al. (1995). "Albumin Binding of Insulins Acylated with Fatty Acids: Characterization of the Lignad-Protein Interaction and Correclation Between Binding Affinity and Timing of the Insulin Effect in vivo," *Biochem. J.* 312:725-731.

Larsen, C.M. et al. (Apr. 12, 2007). "Interleukin-1-Receptor Antagonist in Type 2 Diabetes Mellitus," *The New England Journal of Medicine* 356(15):1517-1526.

Leung, D.W. et al. (Aug. 1989). "A Method for Random Mutagenesis of a Defined DNA Segment Using a Modified Polymerase Chain Reaction," *Technique* 1(1):11-15.

Ling, T.G.I. et al. (1983). "A General Study of the Binding and Separation in Partition Affinity Ligand Assay. Immunoassay of $\beta_2$-Microglobulin," *Journal of Immunological Methods* 59:327-337.

Lovell, D.J. et al. (Apr. 2005). "Interlekin-1 Blockade by Anakinra Improves Clinical Symptoms in Patients With Neonatal-Onset Multisystem Inflammatory Disease," *Arthritis & Rheumatism* 52(4):1283-1286.

Luchansky, J.B. et al. (1988). "Application of Electroporation for Transfer of Plasmid DNA to *Lactobacillus, Lactococcus, Leunconostoc, Listeria, Pediococcus, Bacillus, Staphylococcus, Entercococcus, and Propionibacterium*," Molecular Microbiology 2(5):637-646.

Meziere, C. et al. (1997). "In Vivo T Helper Cell Response to Retro-Iverso Peptidomimetics," *The Journal of Immunology* 159:3230-3237.

Molineux, G. (2003). "Peglyation: Engineering Improved Pharmaceuticals for Enhanced Therapy," *Cancer Treatment Reviews* 28(Suppl. A):13-16.

Nakashima, M. et al. (1999). "In Vitro Characteristics and In Vivo Plasma Disposition of Cisplatin Conjugated with Oxidized and Dicarboxymethylated Dextrans," *Biol. Pharm. Bull.* 22(7):756-761.

Nucci, M.L. et al. (1991). "The Therapeutic Value of Poly(Ethylene Glycol)-Modified Proteins," *Advanced Drug Delivery Reviews* 6:133-151.

Nuki, G. et al. (Nov. 2002). "Long Term Safety and Maintenance of Clinical Improvement Following Treatment With Anakinra (Recombinant Human Interleukin-1 Receptor Antagonist) in Patients With Rheumatoid Arthritis," *Arthritis & Rheumatism* 46(11):2838-2846.

Osborn, B.L. et al (2002). "Albutropin: A Growth Hormone-Albumin Fusion with Improved Pharmacokinetics and Pharmacodynamics in Rats and Monkeys," *European Journal of Pharmacology* 456:149-158.

Osborn, B.L. et al. (2002). "Pharmacokinetic and Pharmacodynamic Studies of Human Serum Albumin-Interferon-α Fusion Protein in Cynomolgus Monkeys," *The Journal of Pharmacology and Experimental Therapeutics* 303(2):540-548.

Pascual, V. et al. (May 2, 2005, e-pub. Apr. 25, 2005). "Role of Interleukin-1 (IL-1) in the Pathogenesis of Systemic Onset Juvenile Idiopathic Arthritis and Clinical Response to IL-1 Blockade," *The Journal of Experimental Medicine* 201 (9):1479-1486.

Pedley, R.B. et al. (1994). "The Potential for Enhanced Tumour Localization by Poly(Ethylene Glycol) Modification of Anti-CEA Antibody," *Br. J. Cancer* 70:1126-1130.

Picker, L.J. et al. (1992). "Physiological and Molecular Mechanisms of Lymphocyte Homing," *Annu. Rev. Immunol.* 10:561-591.

Rich, D.H. (1986). "Inhibitors of Aspartic Proteinases," Chapter 5 *in Proteinase Inhibitors*, Barrett et al. eds, Elsevier Science Publishers BV, pp. 179-217.

Rudinkskaya, A. et al. (Oct. 2003). "Successful Treatment of a Patient With Refractory Adult-Onset Still Disease With Anakinra," *Journal of Clinical Rheumatology* 9(5):330-332.

Ruiz, P.J. et al. (2007, e-pub. Dec. 19, 2006). "Cardiac Death in a Patient with Adult-Onset Still's Disease Treated with the Interleukin 1 Receptor Inhibitor Anakinra," *Ann. Rheum. Dis.* 66:422-423.

Sambrook, J. et al. (2001). *Molecular Cloning: A Laboratory Manual*, Third Edition, Cold Spring Harbor Laboratory Press: Cold Spring Harbor, NY, vol. 2, pp. v-xx, (Table of Contents Only.).

Sato, H. et al. (2002). "Enzymatic Procedure for Site-Specific Peglyation of Proteins," *Advanced Drug Delivery Reviews* 54:487-504.

Satoh, T. et al. (May 2, 1997). "Bioactive Peptide Design Based on Protein Surface Epitopes," *The Journal of Biological Chemistry* 272(18):12715-12180.

Syed, S. et al. (1996). "Inhibition of Thrombin by Hirudin Genetically Fused to Wild-Type or Mutant Antithrombin," *Thrombosis Research* 84(6):419-429.

Thompson, J.D. et al. (1994). "CLUSTAL W: Improving the Sensitivity of Progressive Multiple Sequence Alignment Through Sequence Weighting, Position-Specific Gap Penalties and Weight Matrix Choice," *Nucleic Acids Research* 22(22):4673-4680.

Thorsett, E.D. et al. (Feb. 28, 1983). "Dipeptide Mimics. Conformationally Restricted Inhibitors of Angiotensin-Converting Enzyme," *Biochemical and Biophysical Research Communications* 111(1):166-171.

Vasques, F.M. (2005, e-pub. Sep. 16, 2004). "Refractory Adult Onset Still's Disease Successfully Treated with Anakinra," *Ann. Rheum. Dis.* 64:647-648.

Veber, D.F. et al. (Jun. 1978). "Conformationally Restricted Bicyclic Analogs of Somatostatin," *Proc. Natl. Acad. Sci. USA* 75(6):2636-2640.

Veronese, F.M. et al. (2002). "Introduction and Overview of Peptide and Protein Pegylation," *Advanced Drug Delivery Reviews* 54:453-456.

Veronese, F.M. et al. (Nov. 2005). "PEGylation, Successful Approach to Drug Delivery," *Drug Discovery Today* 10(21):1451-1458.

Wang, Y-S. et al. (2002). "Structural and Biological Characterization of Pegylated Recombinant Interferon Alpha-2b and Its Therapeutic Implications," *Advanced Drug Delivery Reviews* 54:547-570.

Wilkinson, I. et al. (1987). "Tolerogenic Polyethylene Glycol Derivatives of Xenogeneic Monoclonal Immunoglobulins," *Immunology Letters* 15:17-22.

Wulbrand, U. et al. (Feb. 15, 2002). "A Novel Somatostatin Conjugate with a High Affinity to All Five Somatostatin Receptor Subtypes," *Cancer* 94(4):1293-1297.

Yura, H. et al. (1999). "Synthesis and Pharmacokinetics of a Novel Macromolecular Prodrug of Tacrolumus (FK506), FK506-Dextran Conjugate," *Journal of Controlled Release* 57:87-99.

Zalipsky, S. et al. (1992). "Use of Functionalized Poly(Ethylene Glycol)s for Modification of Polypeptides," Chapter 21 *in Poly(Ethylene Glycol) Chemistry: Biotechnical and Biomedical Applications*, Harris, J.M. ed., Plenum Press: NewYork, pp. 347-370.

Zalipsky, S. (1995). "Functionalized Poly(Ethylene Glycol) for Preparation of Biologically Relevant Conjugates," *Bioconjugate Chem.* 6(2):150-165.

\* cited by examiner

FIGURE 2 – continued
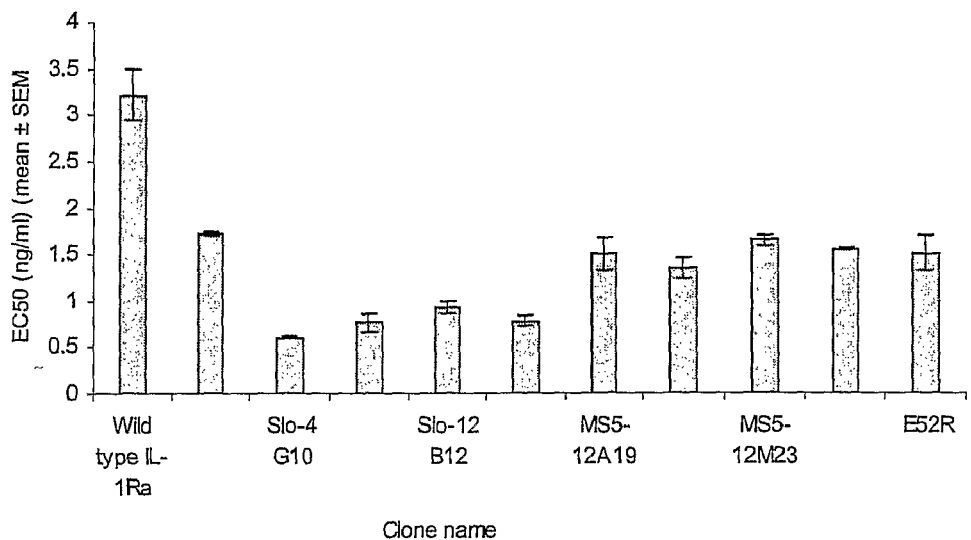
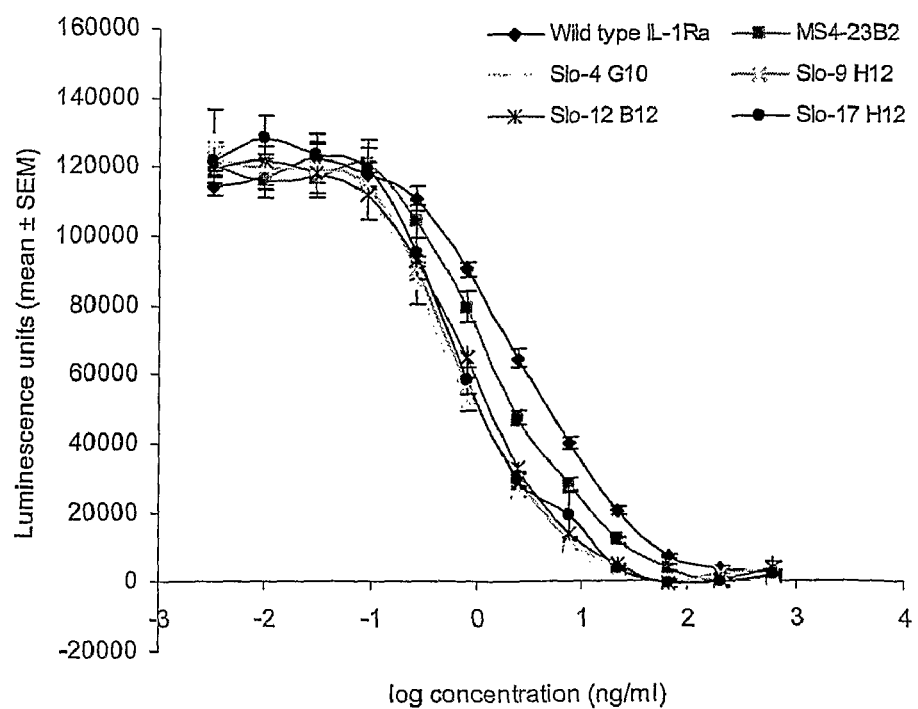

MUTANTS OF INTERLEUKIN-1 RECEPTOR ANTAGONIST

CROSS-REFERENCE TO RELATED APPLICATIONS

This application is a National Phase application under 35 U.S.C.§371 of International Application No. PCT/GB2008/001510 filed May 1, 2008 and claims the benefit of Great Britain Application No. 0708376.9 filed May 1, 2007, the disclosures of which are incorporated herein by reference in their entirety.

FIELD OF INVENTION

The present invention provides agents capable of inhibiting the function of interleukin-1 receptors. In particular, there are provided novel polypeptides and pharmaceutical compositions thereof suitable for use in the treatment of diseases associated with the activation of interleukin-1 receptors.

BACKGROUND

Interleukin-1 Biology

Interleukin-1 (IL-1) is a potent pro-inflammatory cytokine that can be produced by a variety of cell types, including mononuclear phagocytes, in response to infection and inflammation. The IL-1 family consists of two agonists, IL-1α and IL-1β and a naturally occurring receptor antagonist, the IL-1 receptor antagonist (IL-1Ra) (Dinarello, C A, Blood 1996, 87(6): 2095-147). Two IL-1 receptors, IL-1R type I and IL-1R type II, have been identified. Both receptors can interact with all three forms of the IL-1 family molecules. IL-1RI is responsible for mediating IL-1-induced cellular activation. However, the IL-1/IL-1RI complex cannot signal by itself, but is dependent on association with a second receptor chain, IL-1R Accessory Protein (IL-1RAcP) (Dinarello, C A, Blood 1996, 87(6): 2095-147). In contrast to IL-1RI, IL-1RII does not induce cellular activation upon binding to IL-1 and thus IL-1RII functions as regulatory decoy receptor, leading to a net decrease in IL-1 available to bind to IL-1RI.

IL-1Ra is structurally related to IL-1 and is capable of binding to IL-1RI but fails to interact with IL-1RAcP and is thus incapable of inducing cellular activation (Dinarello, C A, Blood 1996, 87(6): 2095-147, Arend, W. P. and C. Gabay, Arthritis Res 2000 2(4): 245-8). Thus, IL-1Ra inhibits the pro-inflammatory effects of IL-1 by functioning as a competitive inhibitor in receptor binding. IL-1Ra has also been shown to bind to IL-1RII but with a lower affinity compared to IL-1.

IL-1 is a potent pro-inflammatory cytokine, which is induced at sites of local infection or inflammation and is involved in the regulation of a variety of physiological and cellular events (summarised in Dinarello C A, CHEST, 2000, 118: 503-508 and Dinarello, C A, Clin Exp Rheumatol, 2002, 20(5 Suppl 27): S1-13). It is capable of activating several cell types including leukocytes and endothelial cells. IL-1 induces and amplifies immunological responses by promoting the production and expression of adhesion molecules, cytokines, chemokines and other inflammatory mediators such as prostaglandin $E_2$ and nitric oxide (NO). As a consequence, local inflammation is amplified and sustained. In addition, the IL-1-induced production of inflammatory mediators results in fever, headache, hypotension and weight loss. Furthermore, IL-1 is a hematopoietic growth factor and has been shown to reduce the nadir of leukocytes and platelets in patients during bone marrow transplantation. IL-1 has also been shown to promote angiogenesis by inducing the production of vascular endothelial growth factor, thereby promoting pannus formation and blood supply in rheumatic joints. Finally, IL-1 has been shown to promote the bone and cartilage degradation in rheumatic diseases.

Role of IL-1 in Disease

Given the vast array of effects on several tissues mediated by IL-1, including its important role as an inflammatory mediator and capability of promoting angiogenesis, IL-1 has been implicated in the pathogenesis of several autoimmune and auto-inflammatory diseases as well as in other disease conditions. Thus, the effect of prevention of the IL-1-IL-1R interaction has been investigated in several indications. In rheumatoid arthritis (RA), treatment with IL-1Ra has been shown to reduce disease severity in several studies (Bresnihan, B., et al., Arthritis Rheum, 1998 41(12): 2196-204, Nuki, G., et al., Arthritis Rheum, 2002. 46(11): 2838-46, Cohen, S., et al., Arthritis Rheum, 2002 46(3): 614-24, Cohen, S. B., et al., Ann Rheum Dis, 2004 63(9):1062-8). Although wild type IL-1Ra was capable of reducing the signs and symptoms of disease, it was less effective than e.g. blockade of the tumour necrosis factor (TNF) pathway in ameliorating disease. The poor efficacy of IL-1Ra in controlling disease severity in RA could potentially be due to an insufficient receptor affinity or plasma half-life of IL-1Ra (Burger D et al., Best Pract Res Clin Rheumatol. 2006 20(5):879-96).

In addition to RA, IL-1R blockade using IL-1Ra has been shown to effectively reduce disease severity in a number of disease conditions. In several indications IL-1Ra treatment rapidly induced complete or near-complete remissions and thus was more effective in amelioration of disease symptoms than in RA. IL-1Ra treatment in systemic onset juvenile idiopathic arthritis (SOJIA) clearly demonstrated that IL-1 plays an important role in pathogenesis (Pascual V et al., J Exp Med, 2005 201(9): 1479-1486). A complete remission was obtained in seven out of nine patients refractory to other therapies and a partial response was seen in the remaining two patients.

In addition, IL-1Ra treatment has shown dramatic effects in amelioration of disease in several auto-inflammatory conditions associated with dysregulated IL-1 production. Familial cold auto-inflammatory syndrome (FCAS), Muckle-Wells disease and neonatal onset multi-system inflammatory disease (NOMID) are all caused by mutations in the CIAS1/NALP3/cryopyrin gene. These mutations result in the over-activation of the inflammasome, resulting in an overproduction of IL-1 (Burger D et al., Best Pract Res Clin Rheumatol. 2006 20(5):879-96). Treatment of patients with IL-1Ra resulted in a dramatic reduction in disease symptoms. Small studies and case reports published for all three diseases demonstrated rapid and complete or near-complete remissions (Hawkins P et al., Arthritis Rheum. 2004 50(2):607-12, Hawkins P et al., N Engl J Med. 2003 Jun. 19; 348(25):2583-4, Boschan et al, Am J Med Genet A, 2006 Apr. 15; 140(8): 883-6, Lovell D J, Arthritis Rheum, 2005 April; 52(4):1283-6 and Hoffman H et al., Lancet. 2004 364(9447):1779-85) clearly demonstrating that IL-1 plays an important role in pathogenesis and that IL-1Ra effectively prevents disease.

Similar to diseases caused by mutations in CIAS1/NALP3/cryopyrin, mutations in the pyrin gene, negatively regulating the inflammasome, also result in dysregulated IL-1 production. Mutations in pyrin are associated with the periodic fever syndrome familial Mediterranean fever (FMF) as well as with pyogenic arthritis pyoderma gangrenosum and acne (PAPA) syndrome. Treatment of a FMF patient resulted in reduction in the systemic inflammatory response (Chae J J et al., Proc Natl Acad Sci USA. 2006 103(26):9982-7). Similarly, a case of IL-1Ra treatment upon knee inflammation flares in a PAPA patient demonstrated rapid and complete resolution of inflammation (Dierselhuis M P et al., *Rheumatology* (Oxford). 2005 44(3):406-8).

Examples of other auto-inflammatory diseases in which IL-1ra treatment has been shown to dramatically reduce disease severity include adult onset Still's disease (Ruiz P J et al., Ann Rheum Dis. 2007 6(3):422-3, Rudinskaya A, J Clin Rheumatol. 2003 9(5):330-2, Vasques Godinho F M et al. *Ann Rheum Dis.* 2005 64(4):647-8, Fitzgerald A A et al., *Arthritis Rheum.* 2005 52(6):1794-803) and hyper-IgD syndrome (Bodar E J et al., *Neth J Med.* 2005 July-August; 63(7):260-4). IL-1 has also been implicated in the pathogenesis of osteoarthritis, and is known to induce proteases involved in cartilage destruction as well as sustaining local inflammation and cartilage erosion. The effect of IL-1Ra treatment was investigated in a small clinical study and demonstrated a beneficial effect in treated patients (Chevalier X, *J Rheumatol,* 2005 32:1317-23).

Finally, the effect of IL-1ra treatment has been investigated in type 2 diabetes mellitus. The rationale behind this is that IL-1Ra production is reduced in pancreatic islets of type 2 diabetes patients. In addition, high glucose has been shown to induce production of IL-1 in pancreatic beta cells, leading to impaired insulin secretion, decreased proliferation and apoptosis. In a clinical trial of 34 IL-1Ra-treated patients and 35 placebo patients, IL-1Ra was shown to improve glycemia and beta cell secretory function as well as to reduce markers of systemic inflammation (Larsen C M et al. *N Engl J Med.* 2007 Apr. 12; 356(15):1517-26).

Importantly, although wild type IL-1Ra treatment has been shown to effectively ameliorate disease, daily injections are required for optimal clinical effects. In addition, withdrawal of treatment results in a rapid disease flare in several indications (Burger D et al., *Best Pract Res Clin Rheumatol.* 2006 20(5):879-96) supporting the notion that the clinical usefulness of wild type IL-1Ra is limited by its short half-life. Thus, an IL-1Ra variant with improved functional activity or enhanced in vivo half-life, resulting in more sustained clinical effect would facilitate less frequent injections or improve pharmaceutical efficacy.

Hence, the present invention seeks to provide improved therapeutic agents for the treatment of diseases associated with interleukin-1 receptor function.

SUMMARY OF THE INVENTION

A first aspect of the invention provides an isolated polypeptide comprising a variant amino acid sequence of SEQ ID NO: 1, or a fusion or derivative of said polypeptide, or a fusion of said derivative thereof, wherein the polypeptide, fusion or derivative retains a biological activity of wild type IL-1Ra.

The amino acid sequences of the polypeptide-based agents of the invention correspond to mutated (non-naturally occurring) forms of the wild type human interleukin-1 receptor antagonist (IL-1Ra), the amino acid sequence of which is shown below in SEQ ID NO: 1:

```
                                              [SEQ ID NO: 1]
  1 RPSGRKSSKM QAFRIWDVNQ KTFYLRNNQL VAGYLQGPNV   40

41 NLEEKIDVVP IEPHALFLGI HGGKMCLSCV KSGDETRLQL   80

81 EAVNITDLSE NRKQDKRFAF IRSDSGPTTS FESAACPGWF  120

121 LCTAMEADQP VSLTNMPDEG VMVTKFYFQE DE          152
```

The wild type human IL-1Ra is expressed initially as a 177-amino acid polypeptide comprising a signal sequence of 25 amino acids at its N-terminus (underlined), as shown below in SEQ ID NO: 2:

```
                                              [SEQ ID NO: 2]
  1 MEICRGLRSH LITLLLFLFH SETICRPSGR KSSKMQAFRI   40

41 WDVNQKTFYL RNNQLVAGYL QGPNVNLEEK IDVVPIEPHA   80

81 LFLGIHGGKM CLSCVKSGDE TRLQLEAVNI TDLSENRKQD  120

121 KRFAFIRSDS GPTTSFESAA CPGWFLCTAM EADQPVSLTN  160

161 MPDEGVMVTK FYFQEDE                           177
```

The term "polypeptide" as used herein takes its conventional meaning, namely a plurality of amino acids that are linked together via a peptide bond.

By "isolated" polypeptide we mean a polypeptide in a form in which it is not found in nature. For example, the polypeptide may be a substantially pure polypeptide produced by recombinant means.

By "biological activity of wild type IL-1Ra" we include the ability to inhibit a function of IL-1 (in either α or β form) and/or its receptor. Thus, we include the ability of wild type IL-1Ra to inhibit an effect mediated by binding of IL-1 to an IL-1 receptor. In particular, we include the ability to inhibit inflammation mediated by IL-1.

In one exemplary embodiment, the polypeptide, fusion or derivative of the invention retains the ability to inhibit, at least in part, the binding of IL-1 to IL-1 receptors.

By "wild type IL-1Ra" we include naturally occurring forms of IL-1Ra, in particular human IL-1Ra as shown in SEQ ID NO: 1 (see also Database Accession No. X52015).

In one embodiment, the polypeptide, fusion or derivative exhibits an enhanced biological activity as compared to wild type IL-1Ra.

By "enhanced" we mean that the biological activity is increased by at least 10% as compared to wild type IL-1Ra, preferably by at least 20%, 30%, 40%, 50%, 60%, 70%, 80%, 90%, 100%, 200%, 300%, 400%, 500%, or 1000% or more.

It will be appreciated by skilled persons that enhanced biological activity as compared to wild type IL-1Ra may manifest itself in a number of ways. For example, the polypeptide, fusion or derivative of the invention may exhibit:

(a) increased binding affinity for IL-1 receptors;
(b) increased binding kinetics, e.g. an increased receptor association rate or decreased receptor dissociation rate;
(c) increased half-life in vivo; and/or
(d) increased epitope specificity, e.g. by the presence of additional binding sites to IL-1 receptors.

In one embodiment, the polypeptide, fusion or derivative of the invention is capable of inhibiting or otherwise interfering, at least in part, with the binding of ligands to interleukin-1 receptors.

For example, the polypeptide, fusion or derivative may be capable of inhibiting the binding of a ligand to an interleukin-1 receptor by at least 10%, for example at least 20%, 30%, 40%, 50%, 60%, 70%, 80%, 90%, 95% or most preferably by 100%.

The term 'ligand' as used herein refers to an atom, ion, or molecule which is able to bind interleukin-1 receptors. Preferably the ligand is a protein, more preferably an interleukin, more preferably still an interleukin-1, most preferably interleukin-1α or interleukin-1β.

Competitive binding may be determined by methods well known to those skilled in the art such as ELISA, immunohistochemistry, immunoprecipitation, Western blots, radiolabelling experiments and other methods known in the art.

IL-1 inhibitory activity of the polypeptide, fusion or derivative of the invention may alternatively be measured by reporter cell assay of inhibition of IL-1β induced NF-☐B activation, inhibition of IL-1β-induced IL-6 production as determined by ELISA, inhibition of disease development in collagen induced arthritis in DBA-1 Janvier mice (see Examples below) and other methods known in the art.

Thus, a polypeptide, fusion or derivative of the invention as defined herein may be tested for an ability to:
(a) inhibit IL-1β-induced NFκB activation in an in vitro reporter assay (see Example II);
(b) inhibit IL-1β-induced production of IL-6 in vitro (see Example III); and/or
(c) inhibit collagen-induced arthritis in mice in vivo (see Example IV).

It will be appreciated by persons skilled in the art that such inhibition may be in whole or in part. Thus, by "inhibit" we include the ability of a polypeptide, fusion or derivative of the invention to reduce one or more of the abovementioned IL-1-mediated biological effects by at least 10% compared to the magnitude of the effect in the absence of the polypeptide, fusion or derivative of the invention.

Thus, the polypeptide, fusion or derivative may be capable of inhibiting IL-1β-induced NFκB activation in an in vitro reporter assay.

Alternatively, or in addition, the polypeptide, fusion or derivative may be capable of inhibiting IL-1β-induced production of IL-6 in vitro.

In one particular embodiment, the polypeptide, fusion or derivative may be capable of inhibiting collagen-induced arthritis in mice in vivo.

As mentioned above, the capacity of a variant, fusion or derivative of wild type IL-1Ra to inhibit the function of IL-1 receptors is likely to be affected by a number of factors, including the binding affinity of the molecule to its interacting counterparts, the epitope specificity that the molecule elicits to other molecules, and its ability to compete with competitive molecules that counteract its intended function.

IL-1Ra has a high affinity for the type I IL-1R, similar to that of IL-1α and IL-1β, and an improvement in this affinity would allow the occupation of IL-1 receptors at low concentrations relative to IL-1α and IL-1β reducing dosage requirements. The association rate of IL-1Ra to IL-1R is lower compared with IL-1β. When IL-1Ra dissociates from its cell receptor, IL-1 rather than IL-1Ra will occupy the empty receptor. An increased association rate, especially relative to that of IL-1, would thus improve the performance of the present invention by increasing the longevity of receptor occupation by variant IL-1Ra. Occupation of IL-1Ra may also protect the variant IL-1Ra from degenerative cellular processes, leading to an increased its half-life. Alternatively, variations in the amino acid sequence may alter the molecule's intrinsic resistance to in vivo degeneration, also producing a longer half-life, thus enabling reduced dosage and frequency of administration.

A change in epitope specificity for the IL-1RI can be an advantage for IL-1Ra. There are two binding sites between IL-1RI and IL-1β, while there is only one binding site between IL-1RI and IL-1Ra. Creating an additional binding site between IL-1RI and IL-1Ra, without establishing a situation that leads to signaling via IL-1RI, would provide a further competitive advantage.

As discussed above, IL-1Ra competes with IL-1β for the binding to the IL-1RI. IL-1β is a molecule of great potency, which needs very few receptors to mediate a cellular response. However, there are also other molecules involved in this signaling network. IL-1RII has been shown to be a natural IL-1 decoy receptor, but it has also been shown to bind IL-1Ra. Although this binding is significantly weaker as compared to the interaction between IL-1 and IL-1RII, elimination of IL-1Ra binding to IL-RII may improve the IL-1 inhibitory effect of IL-1Ra. The IL-1Ra in mice models shows better clinical results than the same molecule in humans. An explanation for this might be that the human IL-1Ra has much lower affinity to the murine IL-1RII than the human counterpart.

Increasing the half-life of a therapeutic protein often implicates increasing its size. This can be accomplished by creating a fusion with another protein or by PEGylation of the molecule. The latter simultaneously also reduces the immunogenicity of the protein.

The IL-1Ra is indeed a small molecule, but the size of the molecule is not always the full explanation for a short plasma half-life. This is illustrated by the distinct difference in plasma half-lives of the anti-TNF therapeutic drugs etanercept (sTNF-RI-Fc) and infliximab (antibody). Although the two molecules are of similar sizes, infliximab has longer plasma half-life. Hence, although one approach to extending in vivo half-life is to improve the mechanistic action of the molecule, another is to alter the size of the molecule.

Human proteins naturally have a greater acceptance in the human body. This can be one explanation why the half-life of Humira, a fully human antibody, is longer than that of Remicade, a humanized, i.e. partly murine, antibody. However, human proteins can also elicit some immunogenicity due to, for example, certain T cell epitopes.

Thus, in one embodiment, the polypeptide, fusion or derivative of the invention is less immunogenic in humans than wild type human IL-1Ra, thereby extending the in vivo half-life.

The term 'immunogenicity' as used herein refers to the capacity of the polypeptide, fusion or derivative to provoke an immune reaction. For example, the polypeptide, fusion or derivative may have reduced immunogenicity compared with IL-1Ra by 10%, 20%, 30%, 40%, 50%, 60%, 70%, 80% or 90% or more compared to that of wild type IL-1Ra.

In one particular embodiment, the polypeptide, fusion or derivative is substantially non-immunogenic.

By "substantially non-immunogenic" we mean that the polypeptide, fusion or derivative does not provoke an immune response when administered to a subject, preferably a human. However, it will be appreciated that a small degree of immunogenicity will be tolerated by subjects. Advantageously, the polypeptide, fusion or derivative does not provoke any clinical symptoms of an immune response, for example induction of neutralising antibodies resulting in lack of efficacy of the polypeptide, fusion or derivative.

It will also be appreciated by skilled persons that it is desirable for the polypeptide, fusion or derivative to retain the biological activity of wild type IL-1Ra in vivo.

In the formulas representing polypeptide embodiments of the present invention, the amino- and carboxy-terminal groups, although often not specifically shown, will be understood to be in the form they would assume at physiological pH values, unless otherwise specified. Thus, the N-terminal $H^{2+}$ and C-terminal $O^-$ at physiological pH are understood to be present though not necessarily specified and shown, either in specific examples or in generic formulas. In the polypeptide notation used herein, the left-hand end of the molecule is the amino terminal end and the right-hand end is the carboxy-terminal end, in accordance with standard usage and convention. The basic and acid addition salts including those which are formed at non-physiological pH values are also included in the polypeptides of the invention.

The term 'amino acid' as used herein includes the standard twenty genetically-encoded amino acids and their corresponding stereoisomers in the 'D' form (as compared to the natural 'L' form), omega-amino acids other naturally-occurring amino acids, unconventional amino acids (e.g. α,α-disubstituted amino acids, N-alkyl amino acids, etc.) and chemically derivatised amino acids (see below).

When an amino acid is being specifically enumerated, such as 'alanine' or 'Ala' or 'A', the term refers to both L-alanine and D-alanine unless explicitly stated otherwise. Other unconventional amino acids may also be suitable components for polypeptides of the present invention, as long as the desired functional property is retained by the polypeptide. For the peptides shown, each encoded amino acid residue, where appropriate, is represented by a single letter designation, corresponding to the trivial name of the conventional amino acid.

In one embodiment, the polypeptides of the invention comprise or consist of L-amino acids.

The polypeptides, and fusions and derivatives thereof, of the invention may be of varying size. Thus, the polypeptide, fusion or derivative may comprise or consist of a polypeptide which is 1000 or fewer amino acids in length, for example 900, 800, 700, 600, 500, 400, 300, 200, 175, 150, 125, 100 or fewer amino acids. In one embodiment, the polypeptide, fusion or derivative comprises or consists of a polypeptide which is between 140 and 180 amino acids in length, for example between 140 and 160 amino acids in length or between 150 and 155 amino acids in length. In one particular embodiment, the polypeptide, fusion or derivative comprises or consists of a polypeptide which is 152 amino acids in length. In an alternative embodiment, the polypeptide, fusion or derivative comprises or consists of a polypeptide which is 153 amino acids in length (for example, a mutated full-length IL-1Ra polypeptide expressed in *E. coli* with an additional N-terminal methionine).

As indicated above, the polypeptides, fusions and derivatives of the present invention correspond to variant or mutated forms of wild type human IL-1Ra (the amino acid sequence of which is depicted in SEQ ID NO: 1) which retain biological activity.

By 'variant' of wild type human IL-1Ra we include polypeptides having insertions, deletions and/or substitutions, either conservative or non-conservative, as compared to the amino acid sequence of SEQ ID NO: 1.

Thus, in one embodiment the polypeptide, fusion or derivative of the invention is or comprises a fragment of the amino acid sequence of SEQ ID NO: 1. In a further embodiment, the polypeptide comprises or consists of at least 10 contiguous amino acid of SEQ ID NO: 1, for example at least 15, 20, 30, 40, 50, 60, 70, 80, 90, 100, 110, 120, 130, 140, 150 or more contiguous amino acids of SEQ ID NO: 1.

It will be appreciated by persons skilled in the art that the term variant is not intended to include a polypeptide consisting of the amino acid sequence of SEQ ID NO: 1 with an additional N-terminal methionine, i.e. Anakinra (Kineret™).

The polypeptide may have an amino acid sequence which has at least 50% identity with the SEQ ID NO. 1, more preferably at least 90%, and most preferably 99.9% identity with the SEQ ID NO. 1, for example at least 60%, 70%, 80%, 90%, 95%, 96%, 97%, 98%, 99% or 99.9%.

The percent sequence identity between two polypeptides may be determined using suitable computer programs, for example the GAP program of the University of Wisconsin Genetic Computing Group and it will be appreciated that percent identity is calculated in relation to polypeptides whose sequences have been aligned optimally.

The alignment may alternatively be carried out using the Clustal W program (as described in Thompson et al., 1994, *Nuc. Acid Res.* 22:4673-4680).

The parameters used may be as follows:
Fast pairwise alignment parameters: K-tuple (word) size; 1, window size; 5, gap penalty; 3, number of top diagonals; 5. Scoring method: x percent.
Multiple alignment parameters: gap open penalty; 10, gap extension penalty; 0.05.
Scoring matrix: BLOSUM.

Alternatively, the BESTFIT program may be used to determine local sequence alignments.

Variants of a known amino acid sequence may be made using the methods well known in the art (for example, as described in *Molecular Cloning: A Laboratory Manual,* 3rd edition, Sambrook & Russell, 2001, Cold Spring Harbor Laboratory Press, the relevant disclosures in which document are hereby incorporated by reference). For example, sequence variation may be introduced using error prone PCR (Leung et al., Technique, 1: 11-15, 1989), the GeneMorph II™ random mutagenesis kit (Stratagene) and other known methods of random mutagenesis, site-directed mutagenesis and protein engineering.

In one particular embodiment, the variants are generated using the methods of FIND® (Fragment INduced Diversity) technology as described in International Patent Applications Nos. WO 2002/48351, WO 03/097834 and PCT/GB2006/004294, which are incorporated herein by reference. This proprietary technology of Alligator Bioscience AB permits control of the degree of variability introduced in selected regions of a parent polynucleotide sequence.

It will be appreciated by persons skilled in the art that the above techniques for generated mutated polypeptides may be used in isolation or in combination. Moreover, these techniques may be used in a single round of mutagenesis or in an iterative process involving several rounds of mutagenesis.

In one embodiment of the first aspect of the invention, the polypeptide, fusion or derivative of the invention exhibits an improved in vivo half-life in humans compared to the wild type IL-1Ra protein (and/or Anakinra [Kineret™]).

Any one or more of the following known methods of improving the half-life of proteins may be used for this purpose:

(a) PEGylation

A widely used method for improving the half-life of proteins is the covalent linking of polyethylene glycol (PEG) moieties to the protein. PEGs are water-soluble polymers that due to their large hydrodynamic volume create a shield around the pegylated drug [Molineux, G., *Pegylation: engineering improved pharmaceuticals for enhanced therapy.* Cancer Treat Rev, 2002. 28 Suppl A: p. 13-6]. Pegylated proteins exhibit a decreased renal clearance and proteolysis, reduced toxicity, reduced immunogenicity and an increased solubility [Veronese, F. M. and J. M. Harris, *Introduction and overview of peptide and protein pegylation.* Adv Drug Deliv Rev, 2002. 54(4): p. 453-6, Chapman, A. P., *PEGylated antibodies and antibody fragments for improved therapy: a review.* Adv Drug Deliv Rev, 2002. 54(4): p. 531-45.]. Pegylation has been employed for several protein-based drugs including the first pegylated molecules asparaginase and adenosine deaminase [Veronese, F. M. and J. M. Harris, *Introduction and overview of peptide and protein pegylation.* Adv Drug Deliv Rev, 2002. 54(4): p. 453-6, Veronese, F. M. and G. Pasut, *PEGylation, successful approach to drug delivery.*

Drug Discov Today, 2005. 10(21): p. 1451-8.].

In order to obtain a successfully pegylated protein, with a maximally increased half-life and retained biological activity, several parameters that may affect the outcome are of importance and should be taken into consideration. The PEG molecules may differ, and PEG variants that have been used for pegylation of proteins include PEG and monomethoxy-PEG. In addition, they can be either linear or branched [Wang, Y. S., et al., *Structural and biological characterization of pegylated recombinant interferon alpha-2b and its therapeutic implications*. Adv Drug Deliv Rev, 2002. 54(4): p. 547-70]. The size of the PEG molecules used may vary and PEG moieties ranging in size between 1 and 40 kDa have been linked to proteins [Wang, Y. S., et al., *Structural and biological characterization of pegylated recombinant interferon alpha-2b and its therapeutic implications*. Adv Drug Deliv Rev, 2002. 54(4): p. 547-70, Sato, H., *Enzymatic procedure for site-specific pegylation of proteins*. Adv Drug Deliv Rev, 2002. 54(4): p. 487-504, Bowen, S., et al., *Relationship between molecular mass and duration of activity of polyethylene glycol conjugated granulocyte colony-stimulating factor mutein*. Exp Hematol, 1999. 27(3): p. 425-32, Chapman, A. P., et al., *Therapeutic antibody fragments with prolonged in vivo half-lives*. Nat Biotechnol, 1999. 17(8): p. 780-3]. In addition, the number of PEG moieties attached to the protein may vary, and examples of between one and six PEG units being attached to proteins have been reported [Wang, Y. S., et al., *Structural and biological characterization of pegylated recombinant interferon alpha-2b and its therapeutic implications*. Adv Drug Deliv Rev, 2002. 54(4): p. 547-70, Bowen, S., et al., *Relationship between molecular mass and duration of activity of polyethylene glycol conjugated granulocyte colony-stimulating factor mutein*. Exp Hematol, 1999. 27(3): p. 425-32]. Furthermore, the presence or absence of a linker between PEG as well as various reactive groups for conjugation have been utilised. Thus, PEG may be linked to N-terminal amino groups, or to amino acid residues with reactive amino or hydroxyl groups (Lys, His, Ser, Thr and Tyr) directly or by using γ-amino butyric acid as a linker. In addition, PEG may be coupled to carboxyl (Asp, Glu, C-terminal) or sulfhydryl (Cys) groups. Finally, Gln residues may be specifically pegylated using the enzyme transglutaminase and alkylamine derivatives of PEG has been described [Sato, H., *Enzymatic procedure for site-specific pegylation of proteins*. Adv Drug Deliv Rev, 2002. 54(4): p. 487-504].

It has been shown that increasing the extent of pegylation results in an increased in vivo half-life. However, it will be appreciated by persons skilled in the art that the pegylation process will need to be optimised for a particular protein on an individual basis.

PEG may be coupled at naturally occurring disulphide bonds as described in WO 2005/007197. Disulfide bonds can be stabilised through the addition of a chemical bridge which does not compromise the tertiary structure of the protein. This allows the conjugating thiol selectivity of the two sulphurs comprising a disulfide bond to be utilised to create a bridge for the site-specific attachment of PEG. Thereby, the need to engineer residues into a peptide for attachment of to target molecules is circumvented.

A variety of alternative block copolymers may also be covalently conjugated as described in WO 2003/059973. Therapeutic polymeric conjugates can exhibit improved thermal properties, crystallisation, adhesion, swelling, coating, pH dependent conformation and biodistribution. Furthermore, they can achieve prolonged circulation, release of the bioactive in the proteolytic and acidic environment of the secondary lysosome after cellular uptake of the conjugate by pinocytosis and more favourable physicochemical properties due to the characteristics of large molecules (e.g. increased drug solubility in biological fluids). Co-block copolymers, comprising hydrophilic and hydrophobic blocks, form polymeric micelles in solution. Upon micelle disassociation, the individual block copolymer molecules are safely excreted.

(b) Fusion Proteins

IgG Fusion Proteins

Human immunoglobulin G (IgG) molecules have circulating half-lives of approximately 20 days. The Fc portion of IgG molecules have been extensively used for the creation of fusion proteins consisting of an Fc part and a protein with a therapeutic use. Such fusion proteins exhibit a prolonged half-life compared to their Fc-lacking counterparts. For example, this strategy was used for the development of etanercept, an anti-rheumatic drug composed of a fusion protein between the soluble human p75 tumour necrosis factor receptor and the Fc portion of human IgG [Goldenberg, M. M., *Etanercept, a novel drug for the treatment of patients with severe, active rheumatoid arthritis*. Clin Ther, 1999. 21(1): p. 75-87; discussion 1-2].

Fc-linked proteins are produced by creating fusion proteins between Fc and the protein of interest by standard genetic engineering protocols. The Fc group is fused to the C-terminus of the protein of interest. Due to the presence of cysteine residues in the hinge region of IgG, Fc fusion proteins are expressed as disulfide-linked homodimers. This further increases their effective size and circulating half-lives. In addition, homodimeric constructs may have an increased functional activity due to improved avidity for its receptor/ligand compared to the corresponding monomeric form.

Human Serum Albumin Fusion Proteins

Human serum albumin (HSA) is the most abundant naturally occurring blood protein in the circulation and has a half-life of 19 days [Osborn, B. L., et al., *Pharmacokinetic and pharmacodynamic studies of a human serum albumin-interferon-alpha fusion protein in cynomolgus monkeys*. J Pharmacol Exp Ther, 2002. 303(2): p. 540-8]. Thus, HSA is a suitable fusion partner for the creation of fusion proteins with improved half-life. HSA fusion proteins exhibit a prolonged half-life due to the capability of HSA to stabilize the protein towards proteolysis and increasing the residence time in the body [Veronese, F. M. and J. M. Harris, *Introduction and overview of peptide and protein pegylation*. Adv Drug Deliv Rev, 2002. 54(4): p. 453-6]. HSA fusion proteins, including IL-2, IFN-α and -β and growth hormone (GH), have been produced and shown to have improved pharmacokinetic properties. Albuferon (HSA-IFN-α) and albutropin (HSA-GH) exhibit half-lives that are 18 and 6 times longer in cynomolgus monkeys, respectively, than the respective counterparts lacking an HSA group [Osborn, B. L., et al., *Pharmacokinetic and pharmacodynamic studies of a human serum albumin-interferon-alpha fusion protein in cynomolgus monkeys*. J Pharmacol Exp Ther, 2002. 303(2): p. 540-8, Osborn, B. L., et al., *Albutropin: a growth hormone-albumin fusion with improved pharmacokinetics and pharmacodynamics in rats and monkeys*. Eur J Pharmacol, 2002. 456(1-3): p. 149-58].

HSA-linked proteins are produced by creating fusion proteins between HSA and the protein of interest by standard genetic engineering protocols. The HSA group may be added at either the N- or the C-terminus. Since the modification is added to the terminus of the protein, the risk of interfering with the structure of the protein and thus with its function is considerably less compared to modifications such as pegylation in the interior of the protein. In addition, the chance of avoiding interference with the active site of the protein is increased by the fact that the HSA group may be added at either the N- or C-terminus of the protein of interest [Osborn, B. L., et al., *Pharmacokinetic and pharmacodynamic studies of a human serum albumin-interferon-alpha fusion protein in cynomolgus monkeys*. J Pharmacol Exp Ther, 2002. 303(2): p. 540-8, Osborn, B. L., et al., *Albutropin: a growth hormone-albumin fusion with improved pharmacokinetics and pharmacodynamics in rats and monkeys*. Eur J Pharmacol, 2002. 456(1-3): p. 149-58, Syed, S., K. E. Kelly, and W. P. Sheffield, *Inhibition of thrombin by hirudin genetically fused to wild-type or mutant antithrombin*. Thromb Res, 1996. 84(6): p. 419-29], depending on which is more likely to result in a fusion protein with maintained biological activity. Thus, in the case of albuferon and albutropin, the C-terminus of the HSA was fused with the N-terminus of IFN-α or GH, respectively, creation of a functionally active hirudin-HSA fusion protein, the HSA group had to be fused to the C-terminus of hirudin. These results indicate that the properties of the target protein determine whether fusion at the N- or C-terminus is optimal.

(c) Glycosylation

The introduction of new sialic acid-containing carbohydrates into a protein (glycoengineering) has been shown to improve in vivo half-life. This method may be used for naturally glycosylated proteins or for proteins that normally lack glycosylation [Elliott, S., et al., *Enhancement of therapeutic protein in vivo activities through glycoengineering*. Nat Biotechnol, 2003. 21(4): p. 414-21].

Glycosylation of proteins may be in the form of N-linked or O-linked carbohydrates. N-linked carbohydrates are typically attached to consensus sequences (Asn-X-Ser/Thr) where X is any amino acid except proline. O-glycosylation occurs at Ser/Thr residues.

For the production of glycosylated proteins, the introduction of novel glycosylation sites may be required. For glycosylation to occur, expression may be performed in yeast, insect or mammalian cell systems. However, the glycosylation pattern in yeast cells is different than mammalian cells, generating hyper-glycosylated proteins, associated with a risk of increased immunogenicity. In contrast, insect cells may be preferred since the glycosylation pattern is similar to that in mammalian cells whereas cell cycles are shorter and therefore expression process faster. Darbepoetin-α is an example of a modified human erythropoetin expressed in CHO cells. It contains two extra N-glycosylation sites, resulting in a three times improved in vivo half-life [Elliott, S., et al., *Enhancement of therapeutic protein in vivo activities through glycoengineering*. Nat Biotechnol, 2003. 21(4): p. 414-21].

An alternative method of glycosylation is the chemical addition of carbohydrate groups to proteins. In this method, the protein is expressed naked, e.g. in *E. coli*. Following expression and purification, the protein is glycosylated in a fully synthetic cell-free process. The method offers great flexibility in terms of number, size and type of carbohydrate to be added.

(d) Fatty Acid Acylation/Myristoylation

Fatty acids have a high affinity and high capacity of HSA binding. This characteristic can be utilized for improving the half-life of proteins. Thus, fatty acyl can be attached to amino acids of proteins, thus generating fatty acyl acylated proteins. Upon reaching the circulation, the fatty acyl group is capable of binding to circulating HSA, resulting in an improved in vivo half-life of the protein.

This method was used for the development of Insulin detemir, which was fatty acyl acylated with myristate at $Lys^{B29}$ by treatment of insulin with fatty acid hydroxyl-succinimide esters in dimethyl formamide/DMSO [Kurtzhals, P., et al., *Albumin binding of insulins acylated with fatty acids: characterization of the ligand-protein interaction and correlation between binding affinity and timing of the insulin effect in vivo*. Biochem J, 1995. 312 (Pt 3): p. 725-31, Hamilton-Wessler, M., at al., *Mechanism of protracted metabolic effects of fatty acid acylated insulin, NN304, in dogs: retention of NN304 by albumin*. Diabetologia, 1999. 42(10): p. 1254-63]. This generated an insulin analogue with increased in vivo half-life due to binding of HSA.

(e) Dextran

Dextran results in an immobilization of the protein, resulting in a slow release and thereby improves the half-life of the protein. Dextran-streptokinase, has been marketed in Russia for thrombolytic therapy. In addition, insulin, somatostatin (which is used for therapy and diagnosis of tumours expressing somatostatin receptors) and the ribosome-inactivating drug trichosantin conjugated to dextran, had a significantly improved half-lives [Baudys, M., et al., *Extending insulin action in vivo by conjugation to carboxymethyl dextran*. Bioconjug Chem, 1998. 9(2): p. 176-83, Chan, W. L., et al., *Lowering of trichosanthin immunogenicity by site-specific coupling to dextran*. Biochem Pharmacol, 1999. 57(8): p. 927-34, Wulbrand, U., et al., *A novel somatostatin conjugate with a high affinity to all five somatostatin receptor subtypes*. Cancer, 2002. 94(4 Suppl): p. 1293-7].

In addition to protein-based pharmaceuticals, dextran has been used for improving the half-life of antibiotics and cytotoxic drugs [Yura, H., et al., *Synthesis and pharmacokinetics of a novel macromolecular prodrug of Tacrolimus (FK506), FK506-dextran conjugate*. J Control Release, 1999. 57(1): p. 87-99, Nakashima, M., et al., *In vitro characteristics and in vivo plasma disposition of cisplatin conjugated with oxidized and dicarboxymethylated dextrans*. Biol Pharm Bull, 1999. 22(7): p. 756-61, Kim, D. S., Y. J. Jung, and Y. M. Kim, *Synthesis and properties of dextran-linked ampicillin*. Drug Dev Ind Pharm, 2001. 27(1): p. 97-101].

Dextran conjugation is carried out by reductive amination using periodate-activated dextran or by the use of cyanogens bromide [Wulbrand, U., et al., *A novel somatostatin conjugate with a high affinity to all five somatostatin receptor subtypes*. Cancer, 2002. 94(4 Suppl): p. 1293-7, Kim, D. S., Y. J. Jung, and Y. M. Kim, *Synthesis and properties of dextran-linked ampicillin*. Drug Dev Ind Pharm, 2001. 27(1): p. 97-101]. The dextran used may vary in size, and dextran ranging from 9 to 82 kDa have been used [Kim, D. S., Y. J. Jung, and Y. M. Kim, *Synthesis and properties of dextran-linked ampicillin*. Drug Dev Ind Pharm, 2001. 27(1): p. 97-101, Behe, M., et al., *Biodistribution, blood half-life, and receptor binding of a somatostatin-dextran conjugate*. Med Oncol, 2001. 18(1): p. 59-64].

In addition to improving the half-life of drugs, dextran conjugation may also reduce immunogenicity [Chan, W. L., et al., *Lowering of trichosanthin immunogenicity by site-specific coupling to dextran*. Biochem Pharmacol, 1999. 57(8): p. 927-34].

Thus, in one embodiment of the first aspect of the invention, the polypeptide, fusion or derivative of the invention is or comprises a "fusion" polypeptide.

By 'fusion' of said polypeptide we include a polypeptide fused to any other polypeptide. For example, the said polypeptide may be fused to a polypeptide such as glutathione-S-transferase (GST) or protein A in order to facilitate purification of said polypeptide. Examples of such fusions are well known to those skilled in the art. Similarly, the said polypeptide may be fused to an oligo-histidine tag, such as His6, or to an epitope recognised by an antibody such as the well-known Myc tag epitope. Fusions to any variant or derivative of said polypeptide are also included in the scope of the invention. It will be appreciated that fusions (or variants, derivatives or fusions thereof) which retain or improve desirable properties, such as IL-1R binding properties or in vivo half-life are preferred.

Thus, the fusion may comprise a variant polypeptide of SEQ ID NO: 1 together with a further portion which confers a desirable feature on the said polypeptide of the invention; for example, the portion may useful in detecting or isolating the polypeptide, or promoting cellular uptake of the polypeptide. The portion may be, for example, a biotin moiety, a radioactive moiety, a fluorescent moiety, for example a small fluorophore or a green fluorescent protein (GFP) fluorophore, as well known to those skilled in the art. The moiety may be an immunogenic tag, for example a Myc tag, as known to those skilled in the art or may be a lipophilic molecule or polypeptide domain that is capable of promoting cellular uptake of the polypeptide, as known to those skilled in the art. The moiety may also be an antibody or an antigen-binding fragment thereof, preferably the antibody or antigen-binding fragment thereof is selected from the group consisting of Fv fragments, Fab-like fragments, single variable domains and domain antibodies. Conveniently, the antibody or an antigen-binding fragment thereof is humanised. By "antibody" we include substantially intact antibody molecules, as well as chimaeric antibodies, humanised antibodies, human antibodies (wherein at least one amino acid is mutated relative to the naturally occurring human antibodies), single chain antibodies, bispecific antibodies (for example, with affinity for both hCAP18/LL37 and an EGF receptor), antibody heavy chains, antibody light chains, homodimers and heterodimers of antibody heavy and/or light chains, and antigen binding fragments and derivatives of the same.

By "antigen-binding fragment" we mean a functional fragment of an antibody that is capable of binding to an antigen.

Preferably, the antigen-binding fragment is selected from the group consisting of Fv fragments (e.g. single chain Fv and disulphide-bonded Fv), Fab-like fragments (e.g. Fab fragments, Fab' fragments and F(ab)$_2$ fragments), single variable domains (e.g. V$_H$ and V$_L$ domains) and domain antibodies (dAbs, including single and dual formats [i.e. dAb-linker-dAb]).

Alternatively, the fusion may comprise a high affinity molecule that mimics an antibody (a so-called 'affibody') (for example, see U.S. Pat. No. 5,831,012 and www.affibody.se). These ligands are small, simple proteins composed of a three-helix bundle based on the scaffold of one of the IgG-binding domains of Protein A (a surface protein from the bacterium *Staphylococcus aureus*). This scaffold has excellent features as an affinity ligand and can be designed to bind with high affinity to any given target protein.

In a further embodiment of the first aspect of the invention, the polypeptide, fusion or derivative of the invention is or comprises one or more amino acids which have been modified or derivatised.

In a yet further embodiment of the first aspect of the invention, the polypeptide, fusion or derivative of the invention is PEGylated.

Chemical derivatives of one or more amino acids may be achieved by reaction with a functional side group. Such derivatised molecules include, for example, those molecules in which free amino groups have been derivatised to form amine hydrochlorides, p-toluene sulphonyl groups, carboxybenzoxy groups, t-butyloxycarbonyl groups, chloroacetyl groups or formyl groups. Free carboxyl groups may be derivatised to form salts, methyl and ethyl esters or other types of esters and hydrazides. Free hydroxyl groups may be derivatised to form O-acyl or O-alkyl derivatives. Also included as chemical derivatives are those peptides which contain naturally occurring amino acid derivatives of the twenty standard amino acids. For example: 4-hydroxyproline may be substituted for proline; 5-hydroxylysine may be substituted for lysine; 3-methylhistidine may be substituted for histidine; homoserine may be substituted for serine and ornithine for lysine. Derivatives also include peptides containing one or more additions or deletions as long as the requisite activity is maintained. Other included modifications are amidation, amino terminal acylation (e.g. acetylation or thioglycolic acid amidation), terminal carboxylamidation (e.g. with ammonia or methylamine), and the like terminal modifications.

In order to provide improvement in the pharmacokinetics of the polypeptide-based agents described herein, the present invention provides polypeptides that are linked to polymers which provide increased stability and half-life (as described above). The attachment of polymer molecules (e.g. polyethylene glycol; PEG) to proteins is well established and has been shown to modulate the pharmacokinetic properties of the modified proteins. For example, PEG modification of proteins has been shown to alter the in vivo circulating half-life, antigenicity, solubility, and resistance to proteolysis of the protein (Abuchowski et al., *J. Biol. Chem.* 1977, 252: 3578; Nucci et al., *Adv. Drug Delivery Reviews* 1991, 6:133; Francis et al., *Pharmaceutical Biotechnology* Vol. 3 (Borchardt, R. T. ed.); and *Stability of Protein Pharmaceuticals: in vivo Pathways of Degradation and Strategies for Protein Stabilization,* 1991, pp 235-263, Plenum, N.Y.).

Both site-specific and random PEGylation of protein molecules is known in the art (for example, see Zalipsky & Lee, *Poly(ethylene glycol) Chemistry: Biotechnical and Biomedical Applications,* 1992, pp 347-370, Plenum, N.Y.; Goodson & Katre, 1990, *Bio/Technology,* 8:343; Hershfield et al., 1991, *PNAS* 88:7185). More specifically, random PEGylation of polypeptide molecules has been described at lysine residues and thiolated derivatives (Ling & Mattiasson, 1983, *Immunol. Methods* 59: 327; Wilkinson et al., 1987, *Immunol. Letters,* 15: 17; Kitamura et al., 1991, *Cancer Res.* 51:4310; Delgado et al., 1996 *Br. J. Cancer,* 73: 175; Pedley et al., 1994, *Br. J. Cancer,* 70:1126).

Attachment of a PEG polymer to an amino acid residue of a polypeptide may be achieved using several PEG attachment moieties including, but not limited to N-hydroxylsuccinimide (NHS) active ester, succinimidyl propionate (SPA), maleimide (MAL), vinyl sulfone (VS), or thiol. A PEG polymer, or other polymer, can be linked to a polypeptide at either a predetermined position, or may be randomly linked to the polypeptide molecule. It is preferred, however, that the PEG polymer be linked to a polypeptide at a predetermined position. A PEG polymer may be linked to any residue in the a polypeptide, however, it is preferable that the polymer is linked to either a lysine or cysteine, which is either naturally occurring in the polypeptide, or which has been engineered into the polypeptide, for example, by mutagenesis of a naturally occurring residue in the polypeptide to either a cysteine or lysine. PEG-linkage can also be mediated through a peptide linker attached to a polypeptide. That is, the PEG moiety can be attached to a peptide linker fused to a polypeptide, where the linker provides the site, e.g. a free cysteine or lysine, for PEG attachment.

As used herein, "polymer" refers to a macromolecule made up of repeating monomeric units, and can refer to a synthetic or naturally occurring polymer such as an optionally substituted straight or branched chain polyalkylene, polyalkenylene, or polyoxyalkylene polymer or a branched or unbranched polysaccharide. A "polymer" as used herein, specifically refers to an optionally substituted or branched chain poly(ethylene glycol), poly(propylene glycol), or poly(vinyl alcohol) and derivatives thereof.

Thus, "PEG" or "PEG polymer" refers to polyethylene glycol, and more specifically can refer to a derivitized form of PEG, including, but not limited to N-hydroxylsuccinimide (NHS) active esters of PEG such as succinimidyl propionate, benzotriazole active esters, PEG derivatized with maleimide, vinyl sulfones, or thiol groups. Particular PEG formulations can include PEG-O—$CH_2CH_2CH_2$—$CO_2$—NHS; PEG-O—$CH_2$—NHS; PEG-O—$CH_2CH_2$—$CO_2$—NHS; PEG-S—$CH_2CH_2$—CO—NHS; PEG-$O_2$CNH—CH(R)—$CO_2$—NHS; PEG-NHCO—$CH_2CH_2$—CO—NHS; and PEG-O—$CH_2$—$CO_2$—NHS; where R is $(CH_2)_4)NHCO_2$(mPEG). PEG polymers useful in the invention may be linear molecules, or may be branched wherein multiple PEG moieties are present in a single polymer.

A "sulfhydryl-selective reagent" is a reagent which is useful for the attachment of a PEG polymer to a thiol-containing amino acid. Thiol groups on the amino acid residue cysteine are particularly useful for interaction with a sulfhydryl-selective reagent. Sulfhydryl-selective reagents which are useful for such attachment include, but are not limited to maleimide, vinyl sulfone, and thiol. The use of sulfhydryl-selective reagents for coupling to cysteine residues is known in the art and may be adapted as needed according to the present invention (for example, see Zalipsky, 1995, *Bioconjug. Chem.* 6:150; Greenwald et al., 2000, *Crit. Rev. Ther. Drug Carrier Syst.* 17:101; Herman et al., 1994, *Macromol. Chem. Phys.* 195:203).

The attachment of PEG or another agent, e.g. HSA, to a polypeptide as described herein will preferably not impair the ability of the polypeptide to inhibit the function of IL-1 receptors. That is, the PEG-linked polypeptide or will retain its inhibitory activity relative to a non-PEG-linked counterpart. As used herein, "retains activity" refers to a level of activity of a PEG-linked polypeptide which is at least 10% of the level of activity of a non-PEG-linked polypeptide, preferably at least 20%, 30%, 40%, 50%, 60%, 70%, 80% and up to 90%, preferably up to 95%, 98%, and up to 100% of the activity of a non-PEG-linked polypeptide comprising the same antigen-binding domain or domains. More specifically, the activity of a PEG-linked polypeptide compared to a non-PEG linked polypeptide should be determined on a polypeptide molar basis; that is equivalent numbers of moles of each of the PEG-linked and non-PEG-linked polypeptides should be used in each trial. In determining whether a particular PEG-linked polypeptide "retains activity", it is preferred that the activity of a PEG-linked polypeptide be compared with the activity of the same polypeptide in the absence of PEG.

As used herein, the term "in vivo half-life" refers to the time taken for the serum concentration of a polypeptide, fusion or derivative of the invention to reduce by 50% in vivo, for example due to degradation of the polypeptide and/or clearance or sequestration of the polypeptide by natural mechanisms. The anti polypeptides described herein can be stabilized in vivo and their half-life increased by binding to molecules, such as PEG, which resist degradation and/or clearance or sequestration. The half-life of a polypeptide is increased if its functional activity persists, in vivo, for a longer period than a similar polypeptide which is not linked to a PEG polymer. Typically, the half life of a PEGylated polypeptide is increased by 10%, 20%, 30%, 40%, 50% or more relative to a non-PEGylated polypeptide. Increases in the range of 2×, 3×, 4×, 5×, 10×, 20×, 30×, 40×, 50× or more of the half life are possible. Alternatively, or in addition, increases in the range of up to 30×, 40×, 50×, 60×, 70×, 80×, 90×, 100×, 150× of the half life are possible.

As used herein, "resistant to degradation" or "resists degradation" with respect to a PEG or other polymer-linked polypeptide means that the PEG- or other polymer-linked polypeptide is degraded by no more than 10% when exposed to pepsin at pH 2.0 for 30 minutes and preferably not degraded at all.

It will be appreciated by persons skilled in the art that peptidomimetic compounds may also be useful in the present invention. Thus, by 'polypeptide' or 'peptide' we include peptidomimetic compounds which are capable of binding to an integrin I-domain. The term 'peptidomimetic' refers to a compound that mimics the conformation and desirable features of a particular peptide as a therapeutic agent.

For example, the polypeptides of the invention include not only molecules in which amino acid residues are joined by peptide (—CO—NH—) linkages but also molecules in which the peptide bond is reversed. Such retro-inverso peptidomimetics may be made using methods known in the art, for example such as those described in Meziere at al. (1997) *J. Immunol.* 159, 3230-3237. This approach involves making pseudopeptides containing changes involving the backbone, and not the orientation of side chains. Retro-inverse peptides, which contain NH—CO bonds instead of CO—NH peptide bonds, are much more resistant to proteolysis.

In an alternative embodiment, the polypeptide of the invention is a peptidomimetic compound wherein one or more of the amino acid residues are linked by a -y($CH_2NH$)— bond in place of the conventional amide linkage.

Similarly, the peptide bond may be dispensed with altogether provided that an appropriate linker moiety which retains the spacing between the carbon atoms of the amino acid residues is used; it is particularly preferred if the linker moiety has substantially the same charge distribution and substantially the same planarity as a peptide bond.

It will be appreciated that the peptide may conveniently be blocked at its N- or C-terminus so as to help reduce susceptibility to exoproteolytic digestion.

A variety of uncoded or modified amino acids such as D-amino acids and N-methyl amino acids have also been used to modify mammalian peptides. In addition, a presumed bioactive conformation may be stabilised by a covalent modification, such as cyclisation or by incorporation of lactam or other types of bridges, for example see Veber at al., 1978, *Proc. Natl. Acad. Sci. USA* 75:2636 and Thursell et al., 1983, *Biochem. Biophys. Res. Comm.* 111:166.

A common theme among many of the synthetic strategies has been the introduction of some cyclic moiety into a peptide-based framework. The cyclic moiety restricts the conformational space of the peptide structure and this frequently results in an increased affinity of the peptide for a particular biological receptor. An added advantage of this strategy is that the introduction of a cyclic moiety into a peptide may also result in the peptide having a diminished sensitivity to cellular peptidases.

Thus, polypeptides of the invention may comprise terminal cysteine amino acids. Such a polypeptide may exist in a heterodetic cyclic form by disulphide bond formation of the mercaptide groups in the terminal cysteine amino acids or in a homodetic form by amide peptide bond formation between the terminal amino acids. As indicated above, cyclising small peptides through disulphide or amide bonds between the N- and C-terminus cysteines may circumvent problems of affinity and half-life sometime observed with linear peptides, by decreasing proteolysis and also increasing the rigidity of the structure, which may yield higher affinity compounds.

Polypeptides cyclised by disulphide bonds have free amino and carboxy-termini which still may be susceptible to proteolytic degradation, while peptides cyclised by formation of an amide bond between the N-terminal amine and C-terminal carboxyl and hence no longer contain free amino or carboxy termini. Thus, the peptides of the present invention can be linked either by a C—N linkage or a disulphide linkage.

Cyclic peptides may have longer half-lives in serum (see, for example, (Picker and Butcher 1992; Huang et al. 1997). The present invention is not limited in any way by the method of cyclisation of peptides, but encompasses peptides whose cyclic structure may be achieved by any suitable method of synthesis. Thus, heterodetic linkages may include, but are not limited to formation via disulphide, alkylene or sulphide bridges. Methods of synthesis of cyclic homodetic peptides and cyclic heterodetic peptides, including disulphide, sulphide and alkylene bridges, are disclosed in U.S. Pat. No. 5,643,872. Other examples of cyclisation methods are discussed and disclosed in U.S. Pat. No. 6,008,058. Cyclic peptides can also be prepared by incorporation of a type 11'β-turn dipeptide (Doyle at al. 1996).

A further approach to the synthesis of cyclic stabilised peptidomimetic compounds is ring-closing metathesis (RCM). This method involves steps of synthesising a peptide precursor and contacting it with an RCM catalyst to yield a conformationally restricted peptide. Suitable peptide precursors may contain two or more unsaturated C—C bonds. The method may be carried out using solid-phase-peptide-synthesis techniques. In this embodiment, the precursor, which is anchored to a solid support, is contacted with a RCM catalyst and the product is then cleaved from the solid support to yield a conformationally restricted peptide.

Another approach, disclosed by D. H. Rich in *Protease Inhibitors*, Barrett and Selveson, eds., Elsevier (1986), has been to design peptide mimics through the application of the transition state analogue concept in enzyme inhibitor design. For example, it is known that the secondary alcohol of staline mimics the tetrahedral transition state of the scissile amide bond of the pepsin substrate.

In summary, terminal modifications are useful, as is well known, to reduce susceptibility by proteinase digestion and therefore to prolong the half-life of the peptides in solutions, particularly in biological fluids where proteases may be present. Polypeptide cyclisation is also a useful modification and is preferred because of the stable structures formed by cyclisation and in view of the biological activities observed for cyclic peptides.

Thus, the polypeptide of the first aspect of the invention may be linear or cyclic.

It will also be appreciated by persons skilled in the art that the polypeptides of the invention may exist in monomeric form or in the form of a multimer thereof (e.g. dimer, trimer, tetramer, pentamer, etc.).

Exemplary polypeptides of the invention are described below.

In one embodiment, the polypeptide, fusion or derivative comprises or consists of a polypeptide variant of amino acid sequence SEQ ID NO: 1 comprising or consisting of substitutions at one or more of amino acid positions 1 to 11, 51 to 56 and/or 89 to 93 relative to SEQ ID NO: 1. These amino acid positions correspond to a 3-dimensional region within the IL-1Ra molecule which participates in receptor interaction. By introducing particular mutations in this region the molecule can be stabilized, thereby facilitating receptor binding.

In a further embodiment, the polypeptide, fusion or derivative comprises or consists of a polypeptide variant of amino acid sequence SEQ ID NO: 1 comprising or consisting of substitutions at one or more of the following amino acid positions:

Q11, V18, N19, Q29, P38, V40, L42, K45, D47, E52, P53, H54, E75, L78, Q79, A82, N84, E90, R92, K93, K96, D104, P107, T109, S110, Q129, M136, D138, V143, K145 and Q149.

It will be appreciated that the above list of substitution sites may be exclusive or non-exclusive. Likewise, the following lists of substitution sites may be exclusive or non-exclusive.

For example, the polypeptide, fusion or derivative may comprise or consist of a polypeptide variant of amino acid sequence SEQ ID NO: 1 comprising or consisting of one or more of the following amino acid substitutions:

Q11R, V18Q, N19F, N19W, N19R, N19K, Q29K, P38Y, P38L, P38Q, P38R, V40I, V40L, L42F, L42W, L42F, K45Q, D47N, D47S, E52K, E52R, P53S, P53T, H54R, E75K, L78F, Q79L, A82T, A82V, N84D, N84S, E90G, E90Y, R92G, K93E, K93Q, K96M, D104Y, P107T, T109I, S110R, Q129L, Q129N, M136K, M136N, M136D, V143I, K145E, Q149K and Q149H.

In the above substitution designations, the number is the residue number in SEQ ID NO: 1 with the preceding letter indicating the amino acid in the wild type sequence and the anteceding letter indicating the amino acid present in the variant sequence (using the conventional single-letter codes for amino acids). Thus, for example, 'P38Y' represents the substitution of amino acid P (proline) at position 38 of SEQ ID NO: 1 with amino acid Y (tyrosine).

In one embodiment, the polypeptide, fusion or derivative comprises or consists of a polypeptide variant of amino acid sequence SEQ ID NO: 1 comprising or consisting of substitutions at one or more of the following amino acid positions:

P38, D47, E52, H54, E75, L78, E90, R92, K93, K96, Q129, M136 and V143.

Thus, the polypeptide, fusion or derivative may comprise or consist of a polypeptide variant of amino acid sequence SEQ ID NO: 1 comprising or consisting of one or more of the following amino acid substitutions:

P38L, P38Y, D47N, E52K, E52R, H54R, E75K, L78F, E90Y, R92G, K93Q, K93E, K96M, Q129L, M136N and V143I.

For example, the polypeptide, fusion or derivative may comprise or consist of a polypeptide variant of amino acid sequence SEQ ID NO: 1 comprising or consisting of one or more of the following amino acid substitutions:

(a) SEQ ID NO: 1 with mutations P38L, D47N, E52R, E75K, R92G, K96M and V143I [Clone name: MS5-12 A19];
(b) SEQ ID NO: 1 with mutations P38L, D47N, E52R, E75K and K93E [Clone name: MS5-30 D10];
(c) SEQ ID NO: 1 with mutations D47N, E52R, L78F and K93E [Clone name: MS5-12 I18];
(d) SEQ ID NO: 1 with mutations E52R and K93Q [Clone name: MS5-12 M23];
(e) SEQ ID NO: 1 with mutations P38Y, D47N, E52R, E90Y and M136N [Clone name: 12B12];
(f) SEQ ID NO: 1 with mutations P38Y, D47N, E52R, H54R, E90Y and M136N [Clone name: 4G10];
(g) SEQ ID NO: 1 with mutations D47N, E52R, H54R and E90Y [Clone name: 9H12];
(h) SEQ ID NO: 1 with mutations D47N, E52R, H54R, E90Y, Q129L and M136N [Clone name: 17H12]; and
(i) SEQ ID NO: 1 with mutations P38L, E52K, E75K, K93Q and V143I [Clone name: MS4-23 B2].

In a further embodiment, the polypeptide, fusion or derivative comprises or consists of a polypeptide variant of amino acid sequence SEQ ID NO: 1 comprising or consisting of substitutions at one or more of the following amino acid positions:

P38, L42, K45, D47, E52, P53, H54, E75, L78, Q79, A82, E90, R92, K93, K96, D104, P107, T109, S110, Q129, M136, D138 and D143.

For example, the polypeptide, fusion or derivative may comprise or consist of a polypeptide variant of amino acid sequence SEQ ID NO: 1 comprising or consisting of a substitution at amino acid position E52.

Thus, the polypeptide, fusion or derivative may comprise or consist of a polypeptide variant of amino acid sequence SEQ ID NO: 1 comprising or consisting of one or more of the following amino acid substitutions:

P38L, P38Y, L42F, K45Q, D47N, D47S, E52K, E52R, P53S, H54R, E75K, L78F, Q79L, A82T, E90G, E90Y, R92G, K93E, K93Q, K96M, D104Y, P107T, T109I, S110R, Q129L, M136N, D138G and D143I.

For example, the polypeptide, fusion or derivative may comprise or consist of a polypeptide variant of amino acid sequence SEQ ID NO: 1 comprising or consisting of one or more of the following amino acid substitutions:

(a) SEQ ID NO: 1 with mutations P38L, D47N, E52K and K93E [Clone name: F1.2.21D23];
(b) SEQ ID NO: 1 with mutations D47N, E52K, E75K and K93Q [Clone name: F1.2.27C21];
(c) SEQ ID NO: 1 with mutations P38L and E52K [Clone name: F1.2.3E8];
(d) SEQ ID NO: 1 with mutations E52R [Clone name: E52R];
(e) SEQ ID NO: 1 with mutations E52K [Clone name: E52K];
(f) SEQ ID NO: 1 with mutations E52K and T109I [Clone name: MS4-39 N20];
(g) SEQ ID NO: 1 with mutations E52K and P107T [Clone name: MS4-45 J23];
(h) SEQ ID NO: 1 with mutations P38L, D47N, E52R, L78F and K93E [Clone name: MS4-19 M1];
(i) SEQ ID NO: 1 with mutations P38L, D47N, E52K, R92G and K93E [Clone name: MS4-30 O8];
(j) SEQ ID NO: 1 with mutations D47N, E52K, H54R, E75K, K93Q [Clone name: MS4-57 H2];
(k) SEQ ID NO: 1 with mutations D47S, E52K, P53S, E75K and K93Q [Clone name: MS4-32 B11];
(l) SEQ ID NO: 1 with mutations P38L, E52K, E75K and K93Q [Clone name: MS4-1 P18];
(m) SEQ ID NO: 1 with mutations P38L, E52K, E75K, K93Q and Q129L [Clone name: MS4-21 B13];
(n) SEQ ID NO: 1 with mutations P38L, E52K, E75K, Q79L and K93Q [Clone name: MS4-29 M18];
(o) SEQ ID NO: 1 with mutations P38L, E52K, E75K, E90G, K93E and D104Y [Clone name: MS4-15 E10];
(p) SEQ ID NO: 1 with mutations P38L, E52K, K93E and K96M [Clone name: MS4-15 B2];
(q) SEQ ID NO: 1 with mutations P38L, E52K, A82T, K93E and S110R [Clone name: MS4-23 C12];
(r) SEQ ID NO: 1 with mutations P38L, D47N, E52K, E75K, K93Q and D138G [Clone name: MS4-22 D21];
(s) SEQ ID NO: 1 with mutations P38L, K45Q, D47N, E52K, E75K, K93Q and V143I [Clone name: MS4-23 D11];
(t) SEQ ID NO: 1 with mutations E52K and K93E [Clone name: MS4-21 C9];
(u) SEQ ID NO: 1 with mutations P38L, E52K, E75K and K93Q [Clone name: MS5-26 M23];
(v) SEQ ID NO: 1 with mutations P38Y, E52R and E90Y [Clone name: 7H8];
(w) SEQ ID NO: 1 with mutations P38Y, E52R, E90Y and M136N [Clone name: 12H8];
(x) SEQ ID NO: 1 with mutations P38Y, E52R, H54R, E90Y and M136N [Clone name: 9E11];
(y) SEQ ID NO: 1 with mutations P38Y, D47N, E52R, E90Y, Q129L and M136N [Clone name: 5B10];
(z) SEQ ID NO: 1 with mutations E52R, E90Y and M136N [Clone name: 3E8]; and
(aa) SEQ ID NO: 1 with mutations P38L, L42F, E52K, E75K, K93Q and M136K [Clone name: MS4-21 A5].

In a further embodiment, the polypeptide, fusion or derivative comprises or consists of a polypeptide variant of amino acid sequence SEQ ID NO: 1 comprising or consisting of substitutions at one or more of the following amino acid positions:

P38, D47, E52, P53, H54, E75, L78, Q79, A82, N84, E90, R92, K93, K96, Q129, M136, V143 and K145

Thus, the polypeptide, fusion or derivative may comprise or consist of a polypeptide variant of amino acid sequence SEQ ID NO: 1 comprising or consisting of one or more of the following amino acid substitutions:

P38L, P38Y, P38Q, D47N, D47S, E52K, E52R, P53T, P53S, H54R, E75K, L78F, Q79L, A82V, N84S, N84D, E90G, E90Y, R92G, K93E, K93Q, K96M, Q129L, M136K, M136N, V143I and K145E.

For example, the polypeptide, fusion or derivative may comprise or consist of a polypeptide variant of amino acid sequence SEQ ID NO: 1 comprising or consisting of one or more of the following amino acid substitutions:

(a) SEQ ID NO: 1 with mutations D47N, E52K, E75K, K93Q and K145E [Clone name: MS4-31 N8];
(b) SEQ ID NO: 1 with mutations P38L, E52K and N84S [Clone name: MS4-20 C18];
(c) SEQ ID NO: 1 with mutations P38L, E52K and K93E [Clone name: MS4-28 C6];
(d) SEQ ID NO: 1 with mutations P38L, D47N, E52R, L78F, K93E and V143I [Clone name: MS5-11 B11];
(e) SEQ ID NO: 1 with mutations P38L, D47N, E52R, R92G, K96M and V143I [Clone name: MS5-21 D8];
(f) SEQ ID NO: 1 with mutations P38L, D47N, E52R, R92G and K96M [Clone name: MS5-21 F6];
(g) SEQ ID NO: 1 with mutations P38L, L78F and K93E [Clone name: MS5-15 E7];
(h) SEQ ID NO: 1 with mutations P38L, D47N, E52R, E75K, L78F and K93E [Clone name: MS5-7 K1];
(i) SEQ ID NO: 1 with mutations P38L, D47N, E52R, E75K and K93Q [Clone name: MS5-23 A11];
(j) SEQ ID NO: 1 with mutations P38L, E52K, R92G and K96M [Clone name: MS5-11 A23];
(k) SEQ ID NO: 1 with mutations P38L, E52K, E75K and K93Q [Clone name: MS5-31 E2];
(l) SEQ ID NO: 1 with mutations P38L, D47S, E52K, P53S, E75K, R92G and K96M [Clone name: MS5-31 C6];
(m) SEQ ID NO: 1 with mutations P38L, R92G and K96M [Clone name: MS5-11 B5];
(n) SEQ ID NO: 1 with mutations D47N, E52R, R92G and K96M, [Clone name: MS5-19 E21];
(o) SEQ ID NO: 1 with mutations E52R, L78F, N84D and K93E [Clone name: MS5-30 H1];
(p) SEQ ID NO: 1 with mutations E52R, E75K, R92G, K96M and V143I [Clone name: MS5-21 C21];
(q) SEQ ID NO: 1 with mutations L78F, A82V, R92G and K96M [Clone name: MS5-17 C22];
(r) SEQ ID NO: 1 with mutations D47S, E52K, P53S, E75K, R92G and K96M [Clone name: MS5-15 C15];

(s) SEQ ID NO: 1 with mutations D47S, E52K, P53S, R92G and K96M [Clone name: MS5-18 A5];
(t) SEQ ID NO: 1 with mutations E75K, R92G, K96M and V143I [Clone name: MS5-27 I13];
(u) SEQ ID NO: 1 with mutations E75K and K93Q [Clone name: MS5-10 A1];
(v) SEQ ID NO: 1 with mutations E75K, E90G, K93Q and V143I [Clone name: MS5-17 C10],
(w) SEQ ID NO: 1 with mutations E75K and K93E [Clone name: MS5-29 B1];
(x) SEQ ID NO: 1 with mutations R92G, K96M and V143I [Clone name: MS5-24 L8];
(y) SEQ ID NO: 1 with mutations R92G and K96M [Clone name: MS5-18 B8];
(z) SEQ ID NO: 1 with mutations P38Y and E52R [Clone name: 7C10];
(aa) SEQ ID NO: 1 with mutations P38Y, E52R and M136N [Clone name: 7A11];
(bb) SEQ ID NO: 1 with mutations P38Y, E90Y and M136N [Clone name: 13C11];
(cc) SEQ ID NO: 1 with mutations P38Y, D47N, E52R and Q129L [Clone name: 1G12];
(dd) SEQ ID NO: 1 with mutations P38Y, H54R, E90Y and Q129L [Clone name: 5G11];
(ee) SEQ ID NO: 1 with mutations P38Y, P53S, Q129L and M136N [Clone name: 8D11];
(ff) SEQ ID NO: 1 with mutations P38Y, D47N, E52R and M136N [Clone name: 12E7];
(gg) SEQ ID NO: 1 with mutations P38Y, E52R, H54R and E90Y [Clone name: 5F10];
(hh) SEQ ID NO: 1 with mutations P38Y, E52R, P53S, Q129L and M136N [Clone name: 1F10];
(ii) SEQ ID NO: 1 with mutations P38Y, P53S, H54R, E90Y and Q129L [Clone name: 8G12];
(jj) SEQ ID NO: 1 with mutations P38Y, P53S, E90Y, Q129L and M136N [Clone name: 12C10];
(kk) SEQ ID NO: 1 with mutations P38Y, D47N, P53S, E90Y and Q129L [Clone name: 4C11];
(ll) SEQ ID NO: 1 with mutations P38Y, D47N, E52R, Q129L and M136N [Clone name: 15H12];
(mm) SEQ ID NO: 1 with mutations P38Y, D47N, H54R, E90Y, Q129L and M136N [Clone name: 5G8];
(nn) SEQ ID NO: 1 with mutations P38Q, E52R and E90Y [Clone name: 7C12];
(oo) SEQ ID NO: 1 with mutations D47N, E90Y, Q129L and M136N [Clone name: 17F12];
(pp) SEQ ID NO: 1 with mutations D47N, P53S, H54R, Q129L and M136N [Clone name: 5F5];
(qq) SEQ ID NO: 1 with mutations D47N, E52R, P53T, H54R, E90Y, Q129L and M136N [Clone name: 17F4];
(rr) SEQ ID NO: 1 with mutations E52R and E90Y [Clone name: 1G10];
(ss) SEQ ID NO: 1 with mutations E52R and H54R [Clone name: 5C8];
(tt) SEQ ID NO: 1 with mutations E52R, H54R, E90Y and M136N [Clone name: 1E12];
(uu) SEQ ID NO: 1 with mutations E52R, H54R, E90Y, Q129L and M136N [Clone name: 8H11];
(vv) SEQ ID NO: 1 with mutations P53S, H54R, E90Y, Q129L and M136N [Clone name: 4E11];
(ww) SEQ ID NO: 1 with mutations E90Y, Q129L and M136N [Clone name: 17C5].

In a further embodiment, the isolated polypeptide, fusion or derivative of the invention may comprise or consist of a polypeptide variant of amino acid sequence SEQ ID NO: 1 comprising or consisting of one or more of the following amino acid substitutions:

Q29K, P38Y, P38R, L42W, D47N, E52R, H54R, E90Y, Q129L, Q129N, M136N, M136D and Q149K.

Thus, the polypeptide may comprise or consist of a polypeptide variant of amino acid sequence SEQ ID NO: 1 comprising or consisting of any permutation (i.e. combination) of one or more of the above mutations.

In one particular embodiment, the polypeptide, fusion or derivative is or comprises one of the above exemplary variant sequences of SEQ ID NO: 1 together with a 6× his tag at its N-terminus.

A second aspect of the invention provides an isolated nucleic acid molecule encoding a polypeptide, fusion or derivative according to the first aspect of the invention.

Thus, the isolated nucleic acid molecule is suitable for expressing a polypeptide, fusion or derivative of the invention. By 'suitable for expressing' is meant that the nucleic acid molecule is a polynucleotide that may be transcribed and/or translated to form the polypeptide, fusion or derivative of the invention. For example, the polynucleotide encoding the polypeptide of the invention may be inserted into an expression vector, such as a plasmid, in proper orientation and correct reading frame for expression. The polynucleotide may be linked to the appropriate transcriptional and translational regulatory control nucleotide sequences recognised by any desired host; such controls may be incorporated in the expression vector.

The nucleic acid molecule of the invention may be DNA or RNA, preferably DNA. The nucleic acid molecule may or may not contain introns in the coding sequence; preferably the nucleic acid molecule is a cDNA.

Generally, the nucleic acid molecule is inserted into an expression vector, such as a plasmid, in proper orientation and correct reading frame for expression. If necessary, the nucleic acid molecule may be linked to the appropriate transcriptional and translational regulatory control nucleotide sequences recognised by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a polynucleotide sequence, with any necessary control elements, that codes for a selectable trait in the transformed cell, such as antibiotic resistance. Alternatively, the gene for such selectable trait can be on another vector, which is used to co-transform the desired host cell.

Host cells that have been transformed by the recombinant nucleic acid molecule of the invention are then cultured for a sufficient time and under appropriate conditions known to those skilled in the art in view of the teachings disclosed herein to permit the expression of the polypeptide, which can then be recovered.

Many expression systems are known, including bacteria (for example *E. coli* and *Bacillus subtilis*), yeasts (for example *Saccharomyces cerevisiae*), filamentous fungi (for example *Aspergillus*), plant cells, mammal cells and insect cells.

The vectors typically include a prokaryotic replicon, such as the ColE1 ori, for propagation in a prokaryote, even if the vector is to be used for expression in other, non-prokaryotic, cell types. The vectors can also include an appropriate promoter such as a prokaryotic promoter capable of directing the expression (transcription and translation) of the genes in a bacterial host cell, such as *E. coli*, transformed therewith. Promoter sequences compatible with exemplary bacterial hosts are typically provided in plasmid vectors containing convenient restriction sites for insertion of a polynucleotide of the present invention.

Typical prokaryotic vector plasmids are pUC18, pUC19, pBR322 and pBR329 available from Biorad Laboratories, (Richmond, Calif., USA) and pTrc99A and pKK223-3 available from Pharmacia, Piscataway, N.J., USA.

A typical mammalian cell vector plasmid is pSVL available from Pharmacia, Piscataway, N.J., USA. This vector uses the SV40 late promoter to drive expression of cloned genes, the highest level of expression being found in T antigen-producing cells, such as COS-1 cells.

An example of an inducible mammalian expression vector is pMSG, also available from Pharmacia. This vector uses the glucocorticoid-inducible promoter of the mouse mammary tumour virus long terminal repeat to drive expression of the cloned gene.

Useful yeast plasmid vectors are pRS403-406 and pRS413-416 and are generally available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers HIS3, TRP1, LEU2 and URA3. Plasmids pRS413-416 are Yeast Centromere plasmids (YCps).

The present invention also relates to a host cell transformed with a polynucleotide vector construct of the present invention. The host cell can be either prokaryotic or eukaryotic. Bacterial cells are preferred prokaryotic host cells and typically are a strain of *E. coli* such as, for example, the *E. coli* strains DH5 available from Bethesda Research Laboratories Inc., Bethesda, Md., USA, and RR1 available from the American Type Culture Collection (ATCC) of Rockville, Md., USA (No ATCC 31343). Preferred eukaryotic host cells include yeast, insect and mammalian cells, preferably vertebrate cells such as those from a mouse, rat, monkey or human fibroblastic and kidney cell lines. Yeast host cells include YPH499, YPH500 and YPH501 which are generally available from Stratagene Cloning Systems, La Jolla, Calif. 92037, USA. Preferred mammalian host cells include Chinese hamster ovary (CHO) cells available from the ATCC as CCL61, NIH Swiss mouse embryo cells NIH/3T3 available from the ATCC as CRL 1658, monkey kidney-derived COS-1 cells available from the ATCC as CRL 1650 and 293 cells which are human embryonic kidney cells. Preferred insect cells are Sf9 cells which can be transfected with baculovirus expression vectors.

Transformation of appropriate cell hosts with a nucleic acid molecule of the present invention is accomplished by well known methods that typically depend on the type of vector used. With regard to transformation of prokaryotic host cells, see for example Sambrook & Russell (supra). Transformation of yeast cells is described in numerous reviews, for example see Gietz & Woods (2001) *Biotechniques* 30:816-228. With regard to vertebrate cells, reagents useful in transfecting such cells, for example calcium phosphate and DEAE-dextran or liposome formulations, are available from Stratagene Cloning Systems, or Life Technologies Inc., Gaithersburg, Md. 20877, USA.

Electroporation is also useful for transforming and/or transfecting cells and is well known in the art for transforming yeast cell, bacterial cells, insect cells and vertebrate cells. For example, many bacterial species may be transformed by the methods described in Luchansky et al. (1988) *Mol. Microbiol.* 2:637-646. Methods for transformation of yeast by electroporation are disclosed in Becker & Guarente (1990) *Methods Enzymol.* 194:182.

Successfully transformed cells, i.e. cells that contain a nucleic acid molecule of the present invention, can be identified by well known techniques. For example, cells resulting from the introduction of an expression construct of the present invention can be grown to produce the polypeptide of the invention. Cells can be harvested and lysed and their DNA content examined for the presence of the DNA using a method such as that described by Sambrook & Russell (supra.). Alternatively, the presence of the protein in the supernatant can be detected using antibodies.

In addition to assaying directly for the presence of recombinant DNA, successful transformation can be confirmed by well known immunological methods when the recombinant DNA is capable of directing the expression of the protein. For example, cells successfully transformed with an expression vector produce proteins displaying appropriate antigenicity. Samples of cells suspected of being transformed are harvested and assayed for the protein using suitable antibodies.

Thus, in a third aspect of the invention provides a vector comprising a nucleic acid molecule according to the second aspect of the invention; preferably the vector is an expression vector.

In one embodiment, the vector is suitable for replication in a eukaryotic cell (for example, a mammalian cell). In an alternative embodiment, the vector is suitable for replication in a prokaryotic cell.

Thus, the vector may be selected from the list consisting of, but not restricted to, pET-3a, pET-3b, pET-3c, pET-3d, pET-9a, pET-9b, pET-9c, pET-9d, pET-11a, pET-11b, pET-11c, pET-11d, pET-12a, pET-12b, pET-12c, pET-14b, pET-15b, pET-16b, pET-17b, pET-17xb, pET-19b, pET-20b(+), pET-21(+), pET-21a(+), pET-21b(+), pET-21c(+), pET-21d(+), pET-22b(+), pET-23(+), pET-23a(+), pET-23b(+), pET-23c(+), pET-23d(+), pET-24(+), pET-24a(+), pET-24b(+), pET-24c(+), pET-24d(+), pET-25b(+), pET-26b(+), pET-27b(+), pET-28a(+), pET-28b(+), pET-28c(+), pET-29a(+), pET-29b(+), pET-29c(+), pET-30 Ek/LIC, pET-30 Xa/LIC, pET-30a(+), pET-30b(+), pET-30c(+), pET-31b(+), pET-32 Ek/LIC, pET-32 Xa/LIC, pET-32a(+), pET-32b(+), pET-32c(+), pET-33b(+), pET-39b(+), pET-40b(+), pET-41a(+), pET-41b(+), pET-41c(+), pET-41 Ek/LIC, pET-42a(+), pET-42b(+), pET-42c(+), pET-43.1a(+), pET-43.1b(+), pET-43.1c(+), pET-43.1 Ek/LIC, pET-44a(+), pET-44b(+), pET-44c(+), pET-44 Ek/LIC, pET-45b(+), pET-46 Ek/LIC, pET-47b(+), pET-48b(+), pET-49b(+), pET-50b(+), pET-51b(+), pET-51b(+) Ek/LIC, pET-52b(+), pET-52b(+) 3C/LIC, pCDNA3.1 (Invitrogen), pLacI, pLysS, pLysE, pLNCX2 (Nolan Laboratory), pTWIN, pShuttle, pUC18, pUC19, pBakPAK, pBR322, pBR329, pTrc99A, pKK233-3, pSVL, pMSG, pRS403, pRS404, pRS405, pRS406, pRS413, pRS414, pRS415 and pRS416.

A fourth aspect of invention provides a host cell comprising a nucleic acid molecule according to the second aspect of the invention or a vector according to the third aspect of the invention.

In one embodiment the host cell is a eukaryotic cell, for example a yeast cell, a filamentous fungi cell, an insect cell, or preferably, mammalian cell.

In an alternative embodiment, the host cell is a prokaryotic cell, for example a bacterial cell.

Thus, the host cell may be selected from the group consisting of, but not limited to *E. coli* strains BL21, BL21(DE3), BL21(DE3)pLysS, C600, CJ236, DH5, DH5alpha, DH5alphaF', ER2566, HB101, JM83, JM101, JM109, LE392, MB408, MC1061, NM522, P2392, PR700, Q358, RR1, TB1, TG1 and Y1088, CHO (Chinese Hamster Ovary) cells (e.g. CCL61), NIH Swiss mouse embryo cells (e.g.

NIH/3T3), COS-1 cells (e.g. CRL 1650 and 293), COS-7 cells (e.g. DSMZ ACC 60) Sf9 cells and yeast cell lines YPH499, YPH500 and YPH501.

In addition to the transformed host cells themselves, the present invention also contemplates a culture of those cells, preferably a monoclonal (clonally homogeneous) culture, or a culture derived from a monoclonal culture, in a nutrient medium.

A fifth aspect of the invention provides a method for making a polypeptide according to the first aspect of the invention, the method comprising culturing a host cell according to the fourth aspect of the invention which expresses the polypeptide, and isolating the polypeptide therefrom.

Methods of cultivating host cells and isolating recombinant proteins therefrom are well known in the art (for example, see Sambrook & Russell, 2001, supra).

A sixth aspect of the invention provides a method for making a polypeptide according to the first aspect of the invention comprising solid phase synthesis of the polypeptide. For example, the polypeptides may be synthesized as described in *Solid-Phase Peptide Synthesis* (1997) Fields, Abelson & Simon (Eds), Academic Press (ISBN: 0-12-182190-0).

A seventh aspect of the invention provides a pharmaceutical formulation comprising a polypeptide according to the first aspect of the invention in admixture with a pharmaceutically or veterinarily acceptable adjuvant, diluent or carrier.

The present invention also includes compositions comprising pharmaceutically acceptable acid or base addition salts of the polypeptides of the present invention. The acids which are used to prepare the pharmaceutically acceptable acid addition salts of the aforementioned base compounds useful in this invention are those which form non-toxic acid addition salts, i.e. salts containing pharmacologically acceptable anions, such as the hydrochloride, hydrobromide, hydroiodide, nitrate, sulphate, bisulphate, phosphate, acid phosphate, acetate, lactate, citrate, acid citrate, tartrate, bitartrate, succinate, maleate, fumarate, gluconate, saccharate, benzoate, methanesulphonate, ethanesulphonate, benzenesulphonate, p-toluenesulphonate and pamoate [i.e. 1,1'-methylene-bis-(2-hydroxy-3 naphthoate)] salts, among others.

Pharmaceutically acceptable base addition salts may also be used to produce pharmaceutically acceptable salt forms of the compounds according to the present invention.

The chemical bases that may be used as reagents to prepare pharmaceutically acceptable base salts of the present compounds that are acidic in nature are those that form non-toxic base salts with such compounds. Such non-toxic base salts include, but are not limited to those derived from such pharmacologically acceptable cations such as alkali metal cations (e.g. potassium and sodium) and alkaline earth metal cations (e.g. calcium and magnesium), ammonium or water-soluble amine addition salts such as N-methylglucamine-(meglumine), and the lower alkanolammonium and other base salts of pharmaceutically acceptable organic amines, among others.

As used herein, 'pharmaceutical formulation' means a therapeutically effective formulation according to the invention.

A 'therapeutically effective amount', or 'effective amount', or 'therapeutically effective', as used herein, refers to that amount which provides a therapeutic effect for a given condition and administration regimen. This is a predetermined quantity of active material calculated to produce a desired therapeutic effect in association with the required additive and diluent, i.e. a carrier or administration vehicle. Further, it is intended to mean an amount sufficient to reduce and most preferably prevent a clinically significant deficit in the activity, function and response of the host. Alternatively, a therapeutically effective amount is sufficient to cause an improvement in a clinically significant condition in a host. As is appreciated by those skilled in the art, the amount of a compound may vary depending on its specific activity. Suitable dosage amounts may contain a predetermined quantity of active composition calculated to produce the desired therapeutic effect in association with the required diluent. In the methods and use for manufacture of compositions of the invention, a therapeutically effective amount of the active component is provided. A therapeutically effective amount can be determined by the ordinary skilled medical or veterinary worker based on patient characteristics, such as age, weight, sex, condition, complications, other diseases, etc., as is well known in the art.

It will be appreciated by persons skilled in the art that the polypeptides, fusions and derivatives of the invention will generally be administered in admixture with a suitable pharmaceutical excipient, diluent or carrier selected with regard to the intended route of administration and standard pharmaceutical practice (for example, see *Remington: The Science and Practice of Pharmacy*, 19th edition, 1995, Ed. Alfonso Gennaro, Mack Publishing Company, Pennsylvania, USA). Suitable routes of administration are discussed below, and include topical, intravenous, oral, pulmonary, nasal, aural, ocular, bladder and CNS delivery.

For example, the polypeptides, fusions and derivatives of the present invention, and pharmaceutical formulations thereof, may be delivered using an injectable sustained-release drug delivery system, such as a microsphere. These are designed specifically to reduce the frequency of injections. An example of such a system is Nutropin Depot which encapsulates recombinant human growth hormone (rhGH) in biodegradable microspheres that, once injected, release rhGH slowly over a sustained period.

Alternatively, the polypeptides, fusions and derivatives of the present invention, and pharmaceutical formulations thereof, can be administered by a surgically implanted device that releases the drug directly to the required site.

Electroporation therapy (EPT) systems can also be employed for the administration of proteins and polypeptides. A device which delivers a pulsed electric field to cells increases the permeability of the cell membranes to the drug, resulting in a significant enhancement of intracellular drug delivery.

Proteins and polypeptides can also be delivered by electroincorporation (EI). EI occurs when small particles of up to 30 microns in diameter on the surface of the skin experience electrical pulses identical or similar to those used in electroporation. In EI, these particles are driven through the stratum corneum and into deeper layers of the skin. The particles can be loaded or coated with drugs or genes or can simply act as "bullets" that generate pores in the skin through which the drugs can enter.

An alternative method of protein and polypeptide delivery is the thermo-sensitive ReGel injectable. Below body temperature, ReGel is an injectable liquid while at body temperature it immediately forms a gel reservoir that slowly erodes and dissolves into known, safe, biodegradable polymers. The active drug is delivered over time as the biopolymers dissolve.

Protein and polypeptide pharmaceuticals can also be delivered orally. One such system employs a natural process for oral uptake of vitamin B12 in the body to co-deliver proteins and polypeptides. By riding the vitamin B12 uptake system, the protein or polypeptide can move through the intestinal wall. Complexes are produced between vitamin B12 analogues and the drug that retain both significant affinity for intrinsic factor (IF) in the vitamin B12 portion of the complex and significant bioactivity of the drug portion of the complex.

Preferably, the pharmaceutical formulation of the present invention is a unit dosage containing a daily dose or unit, daily sub-dose or an appropriate fraction thereof, of the active ingredient. Alternatively, the unit dosage may contain a dose (or sub-dose) for delivery at longer intervals, for example bi-weekly, weekly, bi-monthly, monthly, or longer.

The polypeptides and pharmaceutical formulations of the present invention will normally be administered orally or by any parenteral route, in the form of a pharmaceutical formulation comprising the active ingredient, optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses.

In human therapy, the polypeptides of the invention can be administered alone but will generally be administered in admixture with a suitable pharmaceutical excipient, diluent or carrier selected with regard to the intended route of administration and standard pharmaceutical practice.

For example, the compounds, i.e. polypeptides, of the invention can be administered orally, buccally or sublingually in the form of tablets, capsules, ovules, elixirs, solutions or suspensions, which may contain flavouring or colouring agents, for immediate-, delayed- or controlled-release applications. The compounds of invention may also be administered via intracavernosal injection.

Such tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycolate, croscarmellose sodium and certain complex silicates, and granulation binders such as polyvinylpyrrolidone, hydroxypropy-lmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

The compounds of the invention can also be administered parenterally, for example, intravenously, intra-articularly, intra-arterially, intraperitoneally, intra-thecally, intraventricularly, intrasternally, intracranially, intra-muscularly or subcutaneously, or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

For oral and parenteral administration to human patients, the daily dosage level of the compounds of the invention will usually be from 1 to 1000 mg per adult (i.e. from about 0.015 to 15 mg/kg), administered in single or divided doses.

Thus, for example, the tablets or capsules of the compound of the invention may contain from 1 mg to 1000 mg of active compound for administration singly or two or more at a time, as appropriate. The physician in any event will determine the actual dosage which will be most suitable for any individual patient and it will vary with the age, weight and response of the particular patient. The above dosages are merely exemplary of the average case. There can, of course, be individual instances where higher or lower dosage ranges are merited and such are within the scope of this invention.

The compounds of the invention can also be administered intranasally or by inhalation and are conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A3 or 1,1,1,2,3,3,3-heptafluoropropane (HFA 227EA3), carbon dioxide or other suitable gas. In the case of a pressurised aerosol, the dosage unit may be determined by providing a valve to deliver a metered amount. The pressurised container, pump, spray or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the invention and a suitable powder base such as lactose or starch.

Aerosol or dry powder formulations are preferably arranged so that each metered dose or 'puff' contains at least 1 mg of a compound of the invention for delivery to the patient. It will be appreciated that the overall daily dose with an aerosol will vary from patient to patient, and may be administered in a single dose or, more usually, in divided doses throughout the day.

Alternatively, the compounds of the invention can be administered in the form of a suppository or pessary, or they may be applied topically in the form of a lotion, solution, cream, ointment or dusting powder. The compounds of the invention may also be transdermally administered, for example, by the use of a skin patch. They may also be administered by the ocular route.

For ophthalmic use, the compounds of the invention can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the compounds of the invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouth-washes comprising the active ingredient in a suitable liquid carrier.

Generally, in humans, oral or parenteral administration of the compounds of the invention is the preferred route, being the most convenient.

It will be appreciated by persons skilled in the art that such an effective amount of the polypeptide or formulation thereof may be delivered as a single bolus dose (i.e. acute administration) or, more preferably, as a series of doses over time (i.e. chronic administration).

It will be further appreciated by persons skilled in the art that the polypeptides and pharmaceutical formulations of the present invention have utility in both the medical and veterinary fields. Thus, the methods of the invention may be used in the treatment of both human and non-human animals (such as horses, dogs and cats). Preferably, however, the patient is human.

For veterinary use, a compound of the invention is administered as a suitably acceptable formulation in accordance with normal veterinary practice and the veterinary surgeon will determine the dosing regimen and route of administration which will be most appropriate for a particular animal.

Thus a further embodiment provides a pharmaceutical formulation comprising an amount of a polypeptide of the invention effective to inhibit the function of IL-1 receptors, and a pharmaceutically and biochemically acceptable carrier suitable for parenteral administration in a human.

In an eighth aspect of the invention, there is provided a polypeptide, fusion or derivative according to the first aspect of the invention or a pharmaceutical formulation according to the seventh aspect of the invention for use in medicine.

A ninth aspect of the invention provides the use of a polypeptide, fusion or derivative according to the first aspect of the invention or a pharmaceutical formulation according to the seventh aspect of the invention in the preparation of a medicament for treating a disease or condition capable of being treated by an agent which inhibits the function of IL-1 receptors.

A related aspect of the invention provides a polypeptide, fusion or derivative according to the first aspect of the invention or a pharmaceutical formulation according to the seventh aspect of the invention for treating a disease or condition capable of being treated by an agent which inhibits the function of IL-1 receptors.

Thus, the polypeptides and formulations of the present invention may be used to treat patients or subjects who suffer from or are at risk of suffering from the following conditions or disease states;

Rheumatoid arthritis, all types of juvenile arthritis including systemic onset juvenile idiopathic arthritis (SOJIA), osteoarthritis, familial cold auto-inflammatory syndrome (FCAS), Muckle-Wells disease, neonatal onset multi-system inflammatory disease (NOMID), familial Mediterranean fever (FMF), pyogenic arthritis pyoderma gangrenosum and acne (PAPA) syndrome, adult onset Still's disease, hyper IgD syndrome, type 2 diabetes mellitus, macrophage activation syndrome, TNF receptor-associated periodic syndrome, Blau disease, ankylosing spondylitis, Sweets disease, lupus arthritis, Alzheimer's disease, psoriasis, asthma, atherosclerosis, sarcoidosis, atopic dermatitis, systemic lupus erythematosus, bullous pemphigoid, type I diabetes mellitus, chronic obstructive pulmonary disease, *Helicobacter pylori* gastritis, inflammatory bowel disease (including ulcerative colitis and Crohn's disease), Hepatitis C, ischaemia-reperfusion injury, multiple sclerosis, Neisserial or pneumococcal meningitis, tuberculosis, Bechet's syndrome, septic shock, graft versus host disease, asthma, type I diabetes, Alzheimer's disease, atherosclerosis, adult T cell leukemia, multiple myeloma, periodontitis, obesity and obesity-related diseases (for example, metabolic syndrome, cardiomegaly, congestive heart failure, varicose veins, polycystic ovarian syndrome, gastroesophageal reflux disease (GERD), fatty liver disease, colorectal cancer, breast cancer, uterine cancer, chronic renal failure, stroke and hyperuricemia), intervertebral disc disease, irritable bowel syndrome, Schnitzler syndrome, allergy/atopic dermatitis and gout.

A tenth aspect of the invention provides a method of treating a patient in need of modulation of the function IL-1 receptors, the method comprising administering to the patient an effective amount of a polypeptide according to the first aspect of the invention or a pharmaceutical formulation according to the seventh aspect of the invention.

By 'treatment' we include both therapeutic and prophylactic treatment of the patient. The term 'prophylactic' is used to encompass the use of a polypeptide or formulation described herein which either prevents or reduces the likelihood of a condition or disease state in a patient or subject.

As discussed above, the term 'effective amount' is used herein to describe concentrations or amounts of compounds according to the present invention which may be used to produce a favourable change in a disease or condition treated, whether that change is a remission, a favourable physiological result, a reversal or attenuation of a disease state or condition treated, the prevention or the reduction in the likelihood, of a condition or disease state occurring, depending upon the disease or condition treated. Where polypeptides of the invention are used in combination, each of the polypeptides may be used in an effective amount, wherein an effective amount may include a synergistic amount.

Preferably, the method of the tenth aspect of the invention comprises treating a patient suffering from a disease or condition selected from the following group:

Rheumatoid arthritis, all types of juvenile arthritis including systemic onset juvenile idiopathic arthritis (SOJIA), osteoarthritis, familial cold auto-inflammatory syndrome (FCAS), Muckle-Wells disease, neonatal onset multi-system inflammatory disease (NOMID), familial Mediterranean fever (FMF), pyogenic arthritis pyoderma gangrenosum and acne (PAPA) syndrome, adult onset Still's disease, hyper IgD syndrome, type 2 diabetes mellitus, macrophage activation syndrome, TNF receptor-associated periodic syndrome, Blau disease, ankylosing spondylitis, Sweets disease, lupus arthritis, Alzheimer's disease, psoriasis, asthma, atherosclerosis, sarcoidosis, atopic dermatitis, systemic lupus erythematosus, bullous pemphigoid, type I diabetes mellitus, chronic obstructive pulmonary disease, *Helicobacter pylori* gastritis, inflammatory bowel disease (including ulcerative colitis and Crohn's disease), Hepatitis C, ischaemia-reperfusion injury, multiple sclerosis, Neisserial or pneumococcal meningitis, tuberculosis, Bechet's syndrome, septic shock, graft versus host disease, asthma, type I diabetes, Alzheimer's disease, atherosclerosis, adult T cell leukemia, multiple myeloma, periodontitis, obesity and obesity-related diseases (for example, metabolic syndrome, cardiomegaly, congestive heart failure, varicose veins, polycystic ovarian syndrome, gastroesophageal reflux disease (GERD), fatty liver disease, colorectal cancer, breast cancer, uterine cancer, chronic renal failure, stroke and hyperuricemia), intervertebral disc disease, irritable bowel syndrome, Schnitzler syndrome, allergy/atopic dermatitis and gout.

It will be appreciated by persons skilled in the art that the polypeptides and formulations of the invention may be co-administered in combination with one or more known or conventional agents for the treatment of the particular disease or condition. By 'co-administer' it is meant that the present polypeptides are administered to a patient such that the polypeptides as well as the co-administered compound may be found in the patient's body (e.g. in the bloodstream) at the same time, regardless of when the compounds are actually administered, including simultaneously.

For example, the polypeptide or formulation of the invention comprises may be administered in combination with one or more conventional anti-inflammatory agents, including NSAIDs, corticosteroids and DMARDs (BRMs such as antibody therapies (e.g. anti-TNFα antibodies)).

It will also be appreciated by skilled persons that the polypeptides and formulations of the invention may be co-administered in combination with one or more agents that inhibit the function of IL-1 receptors, IL-1RacP, 1RAK-1, 1RAK-2, MyD88, TRAF-6 or NFκB.

For example, the additional agent may be a non-steroidal anti-inflammatory drug (NSAID), which may be selected from the group including but not limited to aspirin, amoxiprin, benorilate, choline magnesium salicylate, difunisal, faislamine, methyl salicylate, salicyl salicylate (salsalate), diclofenac, aceclofenac, acemetacin, bromfenac, etodolac, indometacin, ketorolac, nabumetone, sulindac, tolmetin, ibuprofen, carprofen, fenbufen, fenoprofen, ketoprofen, loxoprofen, naprotexen, tiaprofenic acid, mefenamic acid, meclofenamic acid, tolfenamic acid, phenylbutazone, azapropazone, metamizole, oxyphenbutazone, piroxicam, lornoxicam, meloxicam, tenoxicam, celecoxib, etoricoxib, lum1Racoxib, parecoxib, forecoxib, valdecoxib, nimesulide, licofelone and omega-3 fatty acids.

Alternatively, the additional agent may be a corticosteroid, which may be alclometasone, aldosterone, amcinonide, beclometasone, betamethasone, budesonide, ciclesoinde, clobetasol, clocortolone, cloprednol, cortisone, cortivazol, deflazacort, deoxycorticosterone, desonide, desoximetasone, desoxycortone, dexamethasone, diflorasone, diflorasone, diflucortolone, difluprednate, flucorolone, flurocortisone, fludroxycortide, flumetasone, flunisolide, flucocinolone acetonide, flucocinonide, fluocortin, fluocortolone, fluorometholone, fluperolone, fluprednidine, fluticasone, formocortal, halcinonide, halometasone, hydrocortisone, hydrocortisol, hydrocortisome aceponate, hydrocortisone buteprate, hydrocortisone butyrate, loteprednol, medrysone, meprednisone, methylprednisone, methylprednisolone aceponate, mometasone furoate, paramethasone, prednicarbate, prednisone, prednisolone, prednylidene, rimexolone, tixocortol, triamcinolone or ulobetasol.

Alternatively, the additional agent may be disease-modifying antirheumatic drug (DMARD), which may be selected from the group including, but not limited to azathioprine, chloroquinem hydroxyl-chloroquine, cyclosporine A, D-penicillamine, sodium aurothiomalate, auranofin, leflunomide, methotrexate, minocycline, sulfasalazine or biological response modifiers (BRMs). BRMs may be selected from the group including, but not limited to etanercept, infliximab, adalimumab, rituximab, abatacept, or a variant thereof.

BRIEF DESCRIPTION OF THE FIGURES

Exemplary aspects of the invention are described in the following non-limited examples, with reference to the following figures.

The amino acid sequences of exemplary clones tested are shown in Example I.

Data are shown as mean luminescence+standard deviation (SD) of reporter cells incubated with IL-1 alone, medium alone (no IL-1), IL-1+library of clones (7392 individual clones), IL-1+selected clones and IL-1+exemplary clone "21D23".

Figure 2:
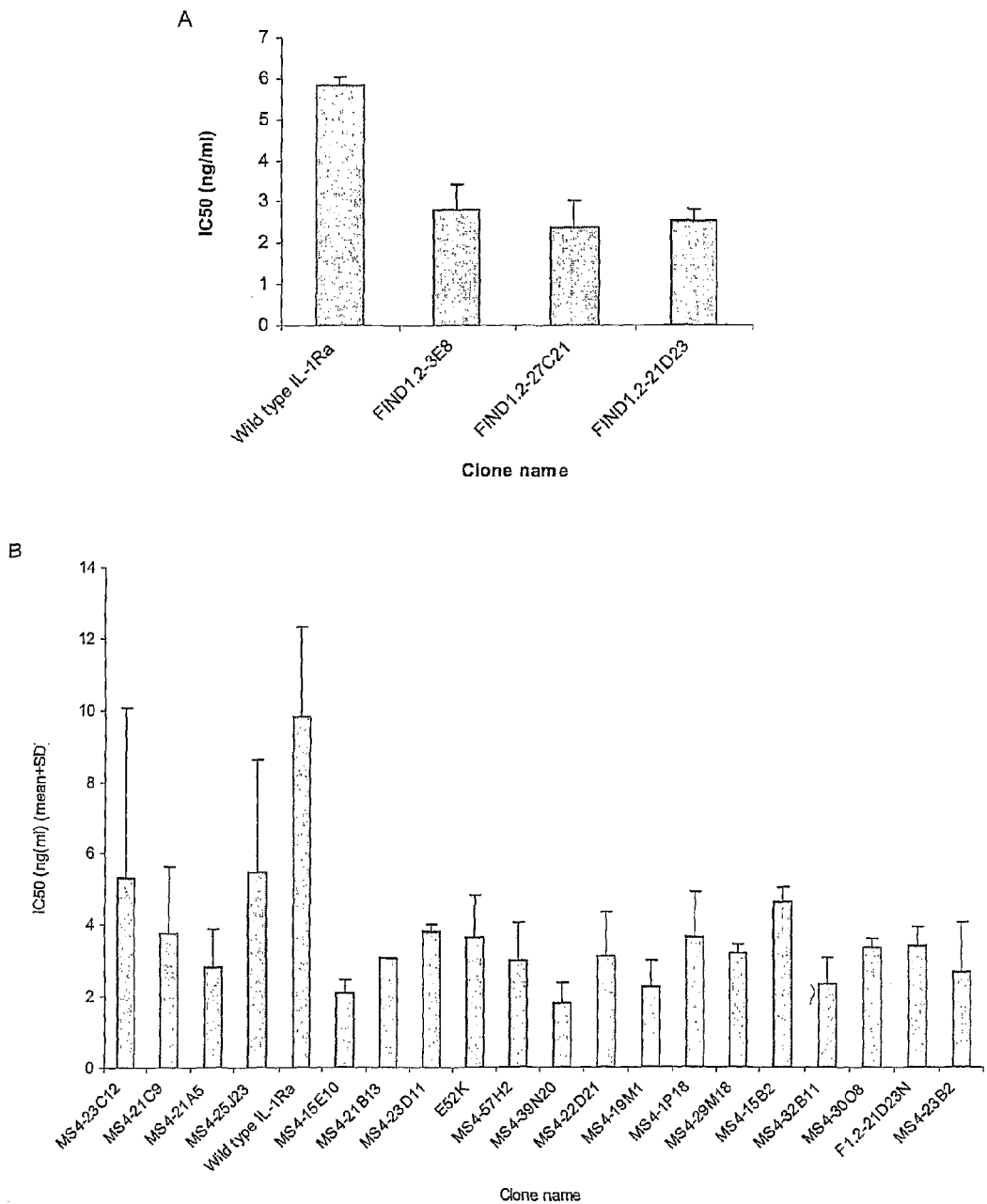

FIG. 2. In vitro inhibition of IL-1β induced activation of NFκB as determined using a reporter cell assay Selected IL-1Ra mutant clones were tested for an ability to inhibit IL-1β induced activation of NFκB, using a reporter cell assay.

(A), (B), (C). The effect of wild type IL-1Ra (i.e. SEQ ID NO: 1) and exemplary IL-1Ra mutant clones was determined in vitro by inhibition of IL-1β induced activation of NFκB using a reporter cell assay. IC50 values were then determined. All IL-1Ra mutant clones comprised an N-terminal 6× his tag. Data are shown as mean+SD.

(D). The effect of wild type IL-1Ra (i.e. SEQ ID NO: 1) and exemplary IL-1Ra mutant clones was determined in vitro by inhibition of IL-1β induced activation of NFκB using a reporter cell assay. Data are shown as mean luminescence±SEM. All IL-1Ra mutant clones comprised an N-terminal 6× his tag.

The amino acid sequences of the clones tested is shown in Example I.

Figure 3A:
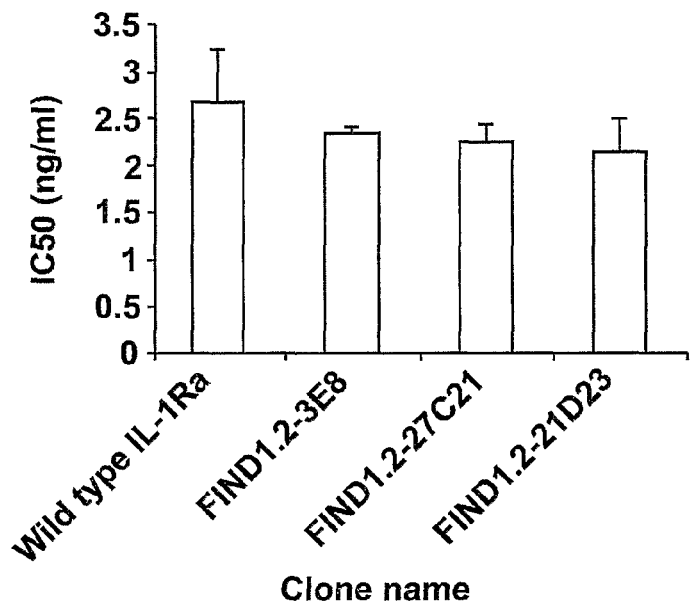
Figure 3B:
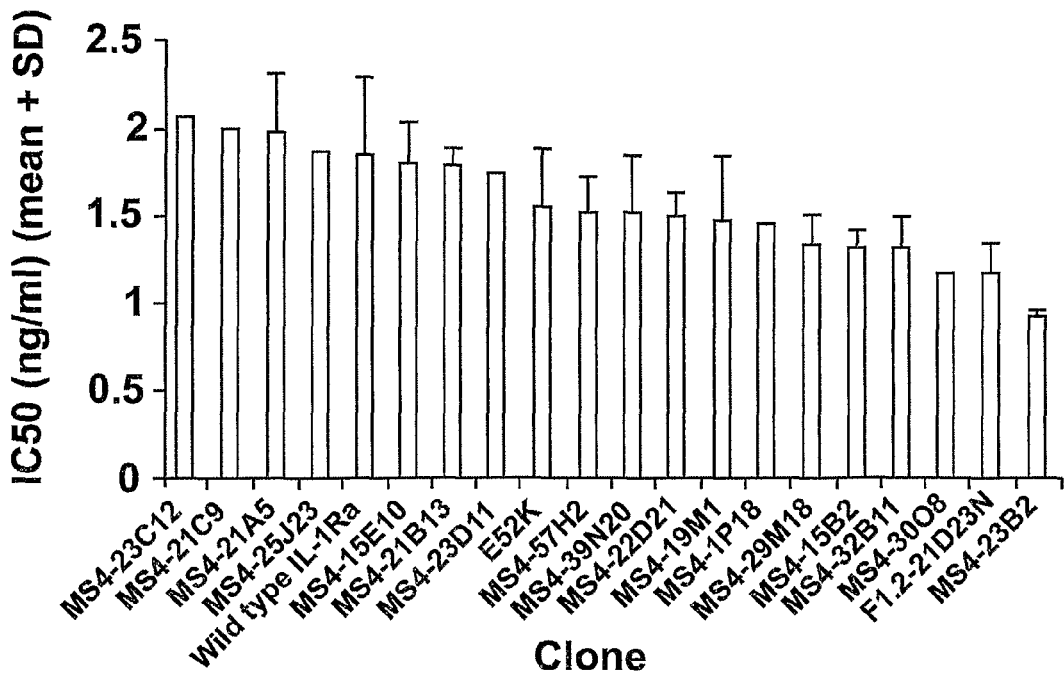

FIG. 3. In vitro inhibition of IL-1β induced IL-6 production by exemplary polypeptides of the invention (A) and (B). The effect of wild type IL-1Ra (i.e. SEQ ID NO: 1) and selected IL-1Ra mutant clones was determined in vitro by inhibition of IL-1β induced IL-6 production. IC50 values were then determined for each clone. All IL-1Ra mutant clones comprised an N-terminal 6× his tag. Data for are shown as mean+SD.

Figure 4:
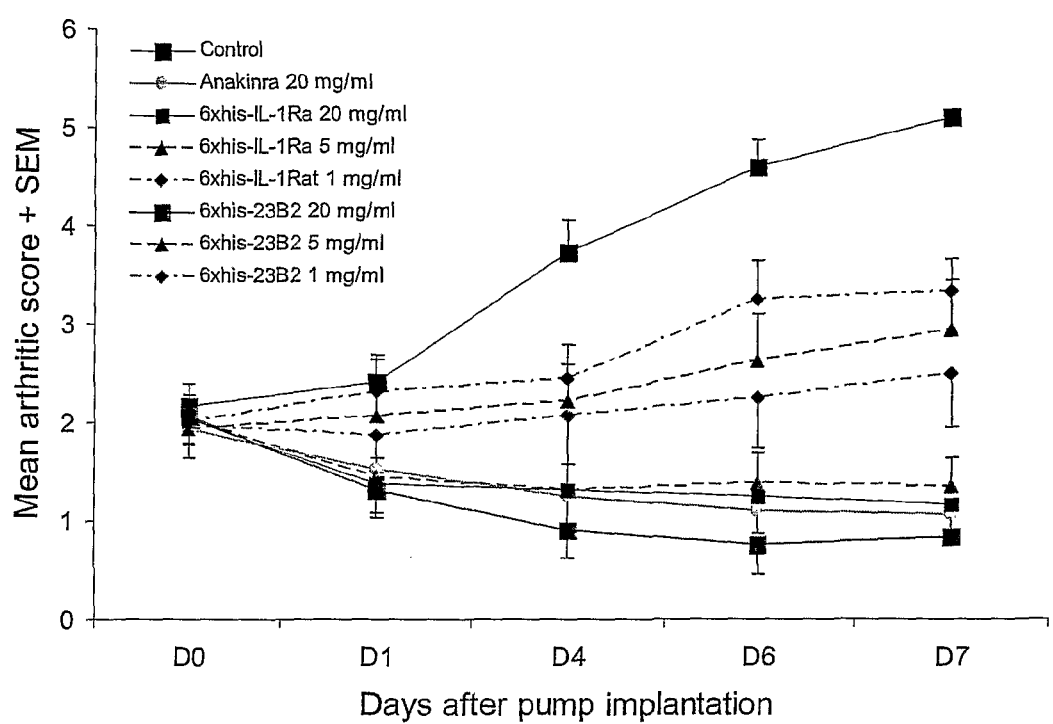

FIG. 4. In vivo inhibition of collagen-induce arthritis in the mouse model

Collagen-induced arthritis was induced in groups of animals (n=8) as described in the Examples. Once the animals had reached a mean score of 2-3, treatment with Anakinra (Kineret™), 6× his-tagged wild type IL-1Ra or 6× his-tagged exemplary clone "23B2" was initiated and disease development determined at day 0, 1, 4, 6 and 7.

Anakinra (Kineret™) corresponds to the wild type IL-1Ra sequence of SEQ ID NO: 1 with an additional N-terminal methionine.

The amino acid sequence of exemplary clone "23B2" is shown in Example I (see "MS4-23 B2").

Results are shown as mean score+SEM.

EXAMPLES

I. Generation of Exemplary Polypeptide Mutants of SEQ ID NO: 1

Materials and Methods

Cloning of IL-1Ra cDNA

Wild type human interleukin-1Ra (IL-1ra) was used as a starting material for subsequent generation of IL-1Ra mutants. The human IL-1Ra wild type protein was retrieved from a liver cDNA library (Clontech) by PCR amplification. Mature IL-1Ra as well as IL-1Ra with signal peptide was cloned into the pGEM vector and confirmed by sequencing.

Expression of IL-1Ra Mutants in COS-7 Cells

Plasmid was prepared from overnight cultures of BL21 (DE3)LysS-vIL-1Ra::pCDNA3.1 using the Montage Plasmid Miniprep$_{HTS}$ Kit (Millipore) according to the manufacturer's instructions. COS-7 cells (ATCC) were transfected with isolated plasmid according to standard protocols (See Ausubel F M et al., Current Protocols in Molecular Biology, 2001). Briefly, 10 µl plasmid preparation (approximately 0.4 µg/ml) was mixed with 0.3 µl Lipofectamine™ 2000 (Invitrogen) and 16 µl Opti-MEM1 (Gibco) according to the manufacturer's instructions and the mixture added to 30,000 COS-7 cells in 50 µl D5 medium (DMEM, Cambrex) supplemented with 5% FBS (heat inactivated at 56° C. for 30 minutes) (Cambrex) and incubated for 72 hours at 37° C. 5% $CO_2$.

Expression of IL1-Ra Mutants in *E. Coli*

A prokaryotic expression system was also used to produce wild type and mutant IL-1Ra. BL21(DE3)pLysS cells (Stratagene) were transformed with the pET22b+ vector (Novagen) containing the individual IL1-Ra alleles according to standard molecular biology techniques (See Ausubel F M et al., Current Protocols in Molecular Biology, 2001). Aseptic cultures were incubated overnight in LB media supplemented with 50 µg/ml ampicillin (amp) and 34 µg/ml chloramphenicol (cam) at 37° C. with shaking. Overnight cultures were diluted 30-fold in LB amp 50 µg/ml and cam 34 µg/ml. 35 µl diluted culture was added to 965 µl LB amp 50 µg/ml and cam 34 µg/ml in deep well plates and incubated at 37° C. with shaking to $OD_{600}$ 0.5 whereupon expression of IL-1Ra alleles was induced by the addition of 1 mM IPTG. Plates were incubated for a further 3 hours at 37° C. with shaking after which cells were centrifuged at 3500 rpm for 10 minutes. Supernatant fluids and cell pellets were retained for later use.

ELISA Quantification of Wild Type and Mutant IL-1Ra

Maxisorp 96-well plates (Nunc) were coated with 0.1 µg/well anti-His antibody (Novagen) in PBS overnight followed by blocking with 200 µl PBS 1% BSA 0.05% Tween-20 per well for 1 hour and washing for 1 hour with (3×) 200 µl PBS 0.05% Tween-20 per well. Samples were diluted 5-fold in PBS 1% BSA 0.05% Tween-20. Anakinra (Kineret™; Amgen) was serial diluted in PBS 1% BSA 0.05% Tween-20 as a protein standard. 100 µl of diluted sample/standard was added in per well in triplicate and incubated for 1 hour. Following washing 3× with 200 µl PBS 0.05% Tween-20 plates were incubated with 100 ul of anti-Anakinra (Kineret™) polyclonal antibody (AB Södra Sandby, Sweden) diluted 2000-fold in PBS 1% BSA 0.05% Tween-20 per well and incubated for 1 hour. After washing 3× with 200 µl PBS 0.05% Tween-20, 100 µl of swine-anti-rabbit-HRP (DAKO), diluted 4000-fold in PBS 1% BSA 0.05% Tween-20 was added per well and plates were incubated for 45 minutes.

After final washing, chromogenic detection was carried out using SIGMA-FAST™ o-phenylenediamine dihydrachioride tablets (SIGMA-Aldrich, St Louis, Mo., USA) according to the manufacturer's instructions. 2 M $H_2SO_4$ was added and the absorbance at 492 nm was measured in a SpectraMax plate reader using the Softmax pro software. All steps were performed at room temperature.

Generation of Variant IL-1Ra Polypeptides by Random Mutagenesis

For the introduction of diversity into the wild type or mutant IL-1Ra gene sequence, random mutagenesis using error prone PCR or the GeneMorphII PCR mutagenesis Kit (Stratagene, cat #200550) was performed according to the manufacturer's instructions.

In the GeneMorphII reactions 1 ng wild type IL-1Ra or 100 pg IL-1Ra mutant gene sequences were used as starting material.

In error prone PCR reactions, the PCR reactions contained 1, 10 or 100 pg cDNA, 7 mM $MgCl_2$, 0.01% gelatine, 0.2 mM dATP, 0.2 mM dGTP, 1 mM dTTP, 1 mM dCTP, 0.3 µM forward primer, 0.3 µM reverse primer, 0.5 mM $MnCl_2$ and 0.025 U AmpliTaq DNA polymerase (Applied Biosystems).

Generation of Variant IL-1Ra Polypeptides by FIND® Technology

FIND® libraries were generated according to the method described in detail in International Patent Applications No. PCT/EP01/14744, WO 03/097834 and PCT/GB2006/004294, which are incorporated herein by reference.

Purification of Wild Type and Mutant IL-1Ra

The IL-1Ra mutants expressed in *E. coli* were purified prior to further analyses. This was performed by using the His-Select iLAP HC Nickel system from Sigma or for larger scale purification, His-trap columns (Amersham Bioscience).

Briefly, the cells from *E. coli* expression were lysed by adding 200 µl/well containing the cells, of a lysis buffer (Complete EDTA-free (Roche), 0.048 U Benzonas (Sigma) and 0.002 U Lysozyme (Novagen) in PBS. The lysate was transferred to His-Select iLAP HC Nickel plates (Sigma) and the plates incubated for three hours in RT with shaking. After washing four times with PBS supplemented with 0.05% Tween-20, and four times with $H_2O$, the samples were eluted with 50 µl of 50 mM Na-phosphate (pH 8.0), 300 mM NaCl and 250 mM Imidazole during 60 minutes at RT with shaking. The samples were then collected and filtered using Multi-Screen Ultracel-10 10,000 NMWL (Millipore) and saved for further analyses.

For large scale purifications (up to 300 mg purified protein), homogenates from *E. coli* cells cultured in a fed batch protocol in a synthetic medium (16.6 g/l $KH_2PO_4$, 4 g/l $(NH_4)_2PO_4$, 1.5 g/l $MgSO_4 \times 7H_2O$, 2.1 g/l citric acid, 74.3 mg/l Fe-citrate, 3.7 mg/l $H_3BO_4$, 18.9 mg/l $MnCl_2 \times 4H_2O$, 10.6 mg/l EDTA, 1.9 mg/l $CuCl_2 \times 2H_2O$, 3.1 mg/l $Na_2MoO_4 \times 2H_2O$, 3.1 mg/l $CoCl2 \times 6H_2O$, 10 mg/l $Zn(CH_3COO)_2 \times 2H_2O$ and 26 g/l glucose) and induced with 1 mM IPTG. Expressed protein was purified using HisTrap™ HP columns (Amersham Bioscience) according to the manufacturer's instructions.

Amino Acid Sequences of Exemplary Mutant IL-1Ra Clones

The above mutagenesis methods were used to generate the variant polypeptides of SEQ ID NO: 1 as defined in Table 1 below, wherein the substitutions are designated with respect to SEQ ID NO: 1. It will be appreciated that the exemplary mutant IL-1Ra polypeptides defined below may comprise an N-terminal 6× histidine tag.

TABLE 1

Exemplary polypeptide mutants of SEQ ID NO: 1

| | M10I | P38L/Y | N39K | L42F | K45Q | D47N/S | P50L | E52K/R | P53S | H54R | A55T | F57L | C66Y/R | S72Y | E75K |
|---|---|---|---|---|---|---|---|---|---|---|---|---|---|---|---|
| Experiment 1 | | | | | | | | | | | | | | | |
| F1.2.21D23 | | L | | | | N | | K | | | | | | | |
| F1.2.27C21 | | | | | | N | | K | | | | | | | X |
| F1.2.3E8 | | L | | | | | | K | | | | | | | |
| E52R | | | | | | | | R | | | | | | | |
| E52K | | | | | | | | K | | | | | | | |
| Experiment 2 | | | | | | | | | | | | | | | |
| MS4-39 N20 | | | | | | | | K | | | | | | | |
| MS4-25 J23 | | | | | | | | K | | | | | | | |
| MS4-19 M1 | | L | | | | N | | R | | | | | | | |
| MS4-30 O8 | | L | | | | N | | K | | | | | | | |
| MS4-31 N8 | | | | | | N | | K | | | | | | | X |
| MS4-57 H2 | | | | | | N | | K | | X | | | | | X |
| MS4-32 B11 | | | | | | S | | K | X | | | | | | X |
| MS4-20 C18 | | L | | | | | | K | | | | | | | |
| MS4-1 P18 | | L | | | | | | K | | | | | | | X |
| MS4-21 A5 | | L | | X | | | | K | | | | | | | X |
| MS4-21 B13 | | L | | | | | | K | | | | | | | X |
| MS4-23 B2 | | L | | | | | | K | | | | | | | X |
| MS4-29 M18 | | L | | | | | | K | | | | | | | X |
| MS4-15 E10 | | L | | | | | | K | | | | | | | X |
| MS4-28 C6 | | L | | | | | | K | | | | | | | |
| MS4-15 B2 | | L | | | | | | K | | | | | | | |
| MS4-23 C12 | | L | | | | | | K | | | | | | | |
| MS4-22 D21 | | L | | | | N | | K | | | | | | | X |
| MS4-23 D11 | | L | | X | | N | | K | | | | | | | X |
| MS4-21 C9 | | L | | | | | | K | | | | | | | |
| Experiment 3 | | | | | | | | | | | | | | | |
| MS5-11 B11 | | L | | | | N | | R | | | | | | | |
| MS5-21 D8 | | L | | | | N | | R | | | | | | | |
| MS5-21 F6 | | L | | | | N | | R | | | | | | | |
| MS5-15 E7 | | L | | | | | | | | | | | | | |
| MS5-12 A19 | | L | | | | N | | R | | | | | | | X |
| MS5-7 K1 | | L | | | | N | | R | | | | | | | X |
| MS5-23 A11 | | L | | | | N | | R | | | | | | | X |
| MS5-30 D10 | | L | | | | N | | R | | | | | | | X |
| MS5-11 A23 | | L | | | | | | K | | | | | | | |
| MS5-31 E2 | | L | | | | | | K | | | | | | | X |
| MS5-26 M23 | | L | | | | | | K | | | | | | | X |
| MS5-31 C6 | | L | | | | S | | K | X | | | | | | X |
| MS5-11 B5 | | L | | | | | | | | | | | | | |
| MS5-12 I18 | | | | | | N | | R | | | | | | | |
| MS5-19 E21 | | | | | | N | | R | | | | | | | |
| MS5-30 H1 | | | | | | | | R | | | | | | | |
| MS5-21 C21 | | | | | | | | R | | | | | | | X |
| MS5-12 M23 | | | | | | | | R | | | | | | | |
| MS5-17 C22 | | | | | | | | | | | | | | | |
| MS5-15 C15 | | | | | | S | | K | X | | | | | | X |
| MS5-18 A5 | | | | | | S | | K | X | | | | | | |
| MS5-27 I13 | | | | | | | | | | | | | | | X |
| MS5-10 A1 | | | | | | | | | | | | | | | X |
| MS5-17 C10 | | | | | | | | | | | | | | | X |
| MS5-29 B1 | | | | | | | | | | | | | | | X |
| MS5-11 B22 | | | | | | | | | | | | | | | X |
| MS5-24 L8 | | | | | | | | | | | | | | | |
| MS5-18 B8 | | | | | | | | | | | | | | | |
| Expt 4 | | | | | | | | | | | | | | | |
| SLO-7C10 | | Y | | | | | | R | | | | | | | |
| SLO-7H8 | | Y | | | | | | R | | | | | | | |
| SLO-7A11 | | Y | | | | | | R | | | | | | | |
| SLO-13C11 | | Y | | | | | | | | | | | | | |
| SLO-1G12 | | Y | | | | N | | R | | | | | | | |
| SLO-5G11 | | Y | | | | | | | | | | X | | | |
| SLO-8D11 | | Y | | | | | | | | X | | | | | |
| SLO-12E7 | | Y | | | | N | | R | | | | | | | |
| SLO-12H8 | | Y | | | | | | R | | | | | | | |
| SLO-5F10 | | Y | | | | | | R | | | | X | | | |
| SLO-1F10 | | Y | | | | | | R | X | | | | | | |
| SLO-8G12 | | Y | | | | | | | | X | | X | | | |
| SLO-9E11 | | Y | | | | | | R | | | | X | | | |
| SLO-12C10 | | Y | | | | | | | | | | | X | | |
| SLO-12B12 | | Y | | | | N | | R | | | | | | | |

TABLE 1-continued

Exemplary polypeptide mutants of SEQ ID NO: 1

| | | | | | |
|---|---|---|---|---|---|
| SLO-4C11 | Y | N | | | X |
| SLO-15H12 | Y | N | R | | |
| SLO-5G8 | Y | N | | | X |
| SLO-5B10 | Y | N | R | | |
| SLO-4G10 | Y | N | R | | X |
| SLO-7C12 | Q | | R | | |
| SLO-9H12 | | N | R | | X |
| SLO-17F12 | | N | | | |
| SLO-5F5 | | N | | X | X |
| SLO-17H12 | | N | R | | X |
| SLO-17F4 | | N | R | T | X |
| SLO-1G10 | | | R | | |
| SLO-5C8 | | | R | | X |
| SLO-3E8 | | | R | | |
| SLO-1E12 | | | R | | X |
| SLO-8H11 | | | R | | X |
| SLO-4E11 | | | | X | X |
| SLO-17C5 | | | | | |

| | R77G | L78F | Q79R/L | A82T/V | N84S/D | S89T | E90G/Y | R92G | K93Q/E | D95G | K96M | A99T | D104G/Y |
|---|---|---|---|---|---|---|---|---|---|---|---|---|---|
| Experiment 1 | | | | | | | | | | | | | |
| F1.2.21D23 | | | | | | | | | E | | | | |
| F1.2.27C21 | | | | | | | | | Q | | | | |
| F1.2.3E8 | | | | | | | | | | | | | |
| E52R | | | | | | | | | | | | | |
| E52K | | | | | | | | | | | | | |
| Experiment 2 | | | | | | | | | | | | | |
| MS4-39 N20 | | | | | | | | | | | | | |
| MS4-25 J23 | | | | | | | | | | | | | |
| MS4-19 M1 | | X | | | | | | | E | | | | |
| MS4-30 O8 | | | | | | | | X | E | | | | |
| MS4-31 N8 | | | | | | | | | Q | | | | |
| MS4-57 H2 | | | | | | | | | Q | | | | |
| MS4-32 B11 | | | | | | | | | Q | | | | |
| MS4-20 C18 | | | | | S | | | | | | | | |
| MS4-1 P18 | | | | | | | | | Q | | | | |
| MS4-21 A5 | | | | | | | | | Q | | | | |
| MS4-21 B13 | | | | | | | | | Q | | | | |
| MS4-23 B2 | | | | | | | | | Q | | | | |
| MS4-29 M18 | | | L | | | | | | Q | | | | |
| MS4-15 E10 | | | | | | | G | | E | | | | Y |
| MS4-28 C6 | | | | | | | | | | | | | |
| MS4-15 B2 | | | | | | | | | E | | X | | |
| MS4-23 C12 | | | | T | | | | | E | | | | |
| MS4-22 D21 | | | | | | | | | Q | | | | |
| MS4-23 D11 | | | | | | | | | Q | | | | |
| MS4-21 C9 | | | | | | | | | E | | | | |
| Experiment 3 | | | | | | | | | | | | | |
| MS5-11 B11 | | X | | | | | | | E | | | | |
| MS5-21 D8 | | | | | | | | X | | | X | | |
| MS5-21 F6 | | | | | | | | X | | | X | | |
| MS5-15 E7 | | X | | | | | | | E | | | | |
| MS5-12 A19 | | | | | | | | X | | | X | | |
| MS5-7 K1 | | X | | | | | | | E | | | | |
| MS5-23 A11 | | | | | | | | | Q | | | | |
| MS5-30 D10 | | | | | | | | | E | | | | |
| MS5-11 A23 | | | | | | | | X | | | X | | |
| MS5-31 E2 | | | | | | | | | Q | | | | |
| MS5-26 M23 | | | | | | | | | Q | | | | |
| MS5-31 C6 | | | | | | | | X | | | X | | |
| MS5-11 B5 | | | | | | | | X | | | X | | |
| MS5-12 I18 | | X | | | | | | | E | | | | |
| MS5-19 E21 | | | | | | | | X | | | X | | |
| MS5-30 H1 | | | | | D | | | | E | | | | |
| MS5-21 C21 | | | | | | | | X | | | X | | |
| MS5-12 M23 | | | | | | | | | Q | | | | |
| MS5-17 C22 | | X | | V | | | | X | | | X | | |
| MS5-15 C15 | | | | | | | | X | | | X | | |
| MS5-18 A5 | | | | | | | | X | | | X | | |
| MS5-27 I13 | | | | | | | | X | | | X | | |
| MS5-10 A1 | | | | | | | | | Q | | | | |
| MS5-17 C10 | | | | | | | G | | Q | | | | |
| MS5-29 B1 | | | | | | | | | E | | | | |
| MS5-11 B22 | | | | | | | | | E | | | | |

TABLE 1-continued

Exemplary polypeptide mutants of SEQ ID NO: 1

| | | | | | | | | | | | | |
|---|---|---|---|---|---|---|---|---|---|---|---|---|
| MS5-24 L8 | | | | | | | | X | X | | | |
| MS5-18 B8 | | | | | | | | X | X | | | |

Expt 4

SLO-7C10
SLO-7H8 — Y
SLO-7A11
SLO-13C11 — Y
SLO-1G12
SLO-5G11 — Y
SLO-8D11
SLO-12E7
SLO-12H8 — Y
SLO-5F10 — Y
SLO-1F10
SLO-8G12 — Y
SLO-9E11 — Y
SLO-12C10 — Y
SLO-12B12 — Y
SLO-4C11 — Y
SLO-15H12
SLO-5G8 — Y
SLO-5B10 — Y
SLO-4G10 — Y
SLO-7C12 — Y
SLO-9H12 — Y
SLO-17F12 — Y
SLO-5F5
SLO-17H12 — Y
SLO-17F4 — Y
SLO-1G10 — Y
SLO-5C8
SLO-3E8 — Y
SLO-1E12 — Y
SLO-8H11 — Y
SLO-4E11 — Y
SLO-17C5 — Y

| | P107T | T109I | S110R | C122G | E126V | Q129L | N135S | M136K/N | D138G | V141L | V143I | K145E |
|---|---|---|---|---|---|---|---|---|---|---|---|---|
| Experiment 1 | | | | | | | | | | | | |
| F1.2.21D23 | | | | | | | | | | | | |
| F1.2.27C21 | | | | | | | | | | | | |
| F1.2.3E8 | | | | | | | | | | | | |
| E52R | | | | | | | | | | | | |
| E52K | | | | | | | | | | | | |
| Experiment 2 | | | | | | | | | | | | |
| MS4-39 N20 | | X | | | | | | | | | | |
| MS4-25 J23 | X | | | | | | | | | | | |
| MS4-19 M1 | | | | | | | | | | | | |
| MS4-30 O8 | | | | | | | | | | | | |
| MS4-31 N8 | | | | | | | | | | | | X |
| MS4-57 H2 | | | | | | | | | | | | |
| MS4-32 B11 | | | | | | | | | | | | |
| MS4-20 C18 | | | | | | | | | | | | |
| MS4-1 P18 | | | | | | | | | | | | |
| MS4-21 A5 | | | | | | | | K | | | | |
| MS4-21 B13 | | | | | | X | | | | | | |
| MS4-23 B2 | | | | | | | | | | | X | |
| MS4-29 M18 | | | | | | | | | | | | |
| MS4-15 E10 | | | | | | | | | | | | |
| MS4-28 C6 | | | | | | | | | | | | |
| MS4-15 B2 | | | | | | | | | | | | |
| MS4-23 C12 | | | X | | | | | | | | | |
| MS4-22 D21 | | | | | | | | | X | | | |
| MS4-23 D11 | | | | | | | | | | | X | |
| MS4-21 C9 | | | | | | | | | | | | |
| Experiment 3 | | | | | | | | | | | | |
| MS5-11 B11 | | | | | | | | | | | X | |
| MS5-21 D8 | | | | | | | | | | | X | |
| MS5-21 F6 | | | | | | | | | | | | |
| MS5-15 E7 | | | | | | | | | | | | |
| MS5-12 A19 | | | | | | | | | | | X | |
| MS5-7 K1 | | | | | | | | | | | | |
| MS5-23 A11 | | | | | | | | | | | | |

TABLE 1-continued

Exemplary polypeptide mutants of SEQ ID NO: 1

| Mutant | Col1 | Col2 | Col3 |
|---|---|---|---|
| MS5-30 D10 | | | |
| MS5-11 A23 | | | |
| MS5-31 E2 | | | |
| MS5-26 M23 | | | |
| MS5-31 C6 | | | |
| MS5-11 B5 | | | |
| MS5-12 I18 | | | |
| MS5-19 E21 | | | |
| MS5-30 H1 | | | |
| MS5-21 C21 | | | X |
| MS5-12 M23 | | | |
| MS5-17 C22 | | | |
| MS5-15 C15 | | | |
| MS5-18 A5 | | | |
| MS5-27 I13 | | | X |
| MS5-10 A1 | | | |
| MS5-17 C10 | | | X |
| MS5-29 B1 | | | |
| MS5-11 B22 | | | |
| MS5-24 L8 | | | X |
| MS5-18 B8 | | | |
| Expt 4 | | | |
| SLO-7C10 | | | |
| SLO-7H8 | | | |
| SLO-7A11 | | N | |
| SLO-13C11 | | N | |
| SLO-1G12 | X | | |
| SLO-5G11 | X | | |
| SLO-8D11 | X | N | |
| SLO-12E7 | | N | |
| SLO-12H8 | | N | |
| SLO-5F10 | | | |
| SLO-1F10 | X | N | |
| SLO-8G12 | X | | |
| SLO-9E11 | | N | |
| SLO-12C10 | X | N | |
| SLO-12B12 | | N | |
| SLO-4C11 | X | | |
| SLO-15H12 | X | N | |
| SLO-5G8 | X | N | |
| SLO-5B10 | X | N | |
| SLO-4G10 | | N | |
| SLO-7C12 | | | |
| SLO-9H12 | | | |
| SLO-17F12 | X | N | |
| SLO-5F5 | X | N | |
| SLO-17H12 | X | N | |
| SLO-17F4 | X | N | |
| SLO-1G10 | | | |
| SLO-5C8 | | | |
| SLO-3E8 | | N | |
| SLO-1E12 | | N | |
| SLO-8H11 | X | N | |
| SLO-4E11 | X | N | |
| SLO-17C5 | X | N | |

II. In Vitro Activity as Determined by Inhibition of IL-1β Induced NF-κB Activation Introduction One method for screening of the libraries of mutant IL-1Ra clones was based on a luciferase assay that measures the capability of each mutant polypeptide to inhibit IL-1β induced NF-κB activation. This reporter cell assay was used to analyze the IL-1β inhibitory effect of the IL-1Ra mutants from culture supernatants of COS-7 cells transiently expressing the mutant polypeptides.

In additional experiments, the IL-1Ra mutants were expressed in and purified from E. coli.

Materials & Methods

Cultures of NIH/3T3 fibroblast reporter cells, which express both IL1-RI and IL-1RII, stably transfected with the construct 5× NFκB luciferase were used as reporter cells. The reporter cells were cultured overnight in D5 media (DMEM, Cambrex) supplemented with 5% (heat inactivated at 56° C. for 30 minutes) (Cambrex) at 37° C., 5% $CO_2$.

Cultures of COS-7 cells transiently expressing IL-1Ra mutant protein were cultured for 72 h in D5 media (DMEM, Cambrex) supplemented with 5% (heat inactivated at 56° C. for 30 minutes) (Cambrex) at 37° C., 5% $CO_2$.

A mixture of supernatant from mutant-expressing COS-7 cells (diluted 100-fold as the final concentration in D5 media) and IL-1β (R&D, final concentration 0.1 ng/ml in D5), was prepared. Alternatively the supernatant from mutant-expressing COS-7 cells could be replaced by purified IL-1Ra mutants expressed from E. coli BL21(DE3)pLysS.

Growth media was fully aspirated from reporter cells and 16 μl of the mutant IL-1Ra/IL-1β mixture was added per well. Plates were incubated at 37° C., 5% $CO_2$ for 4 hours.

Figure 1:
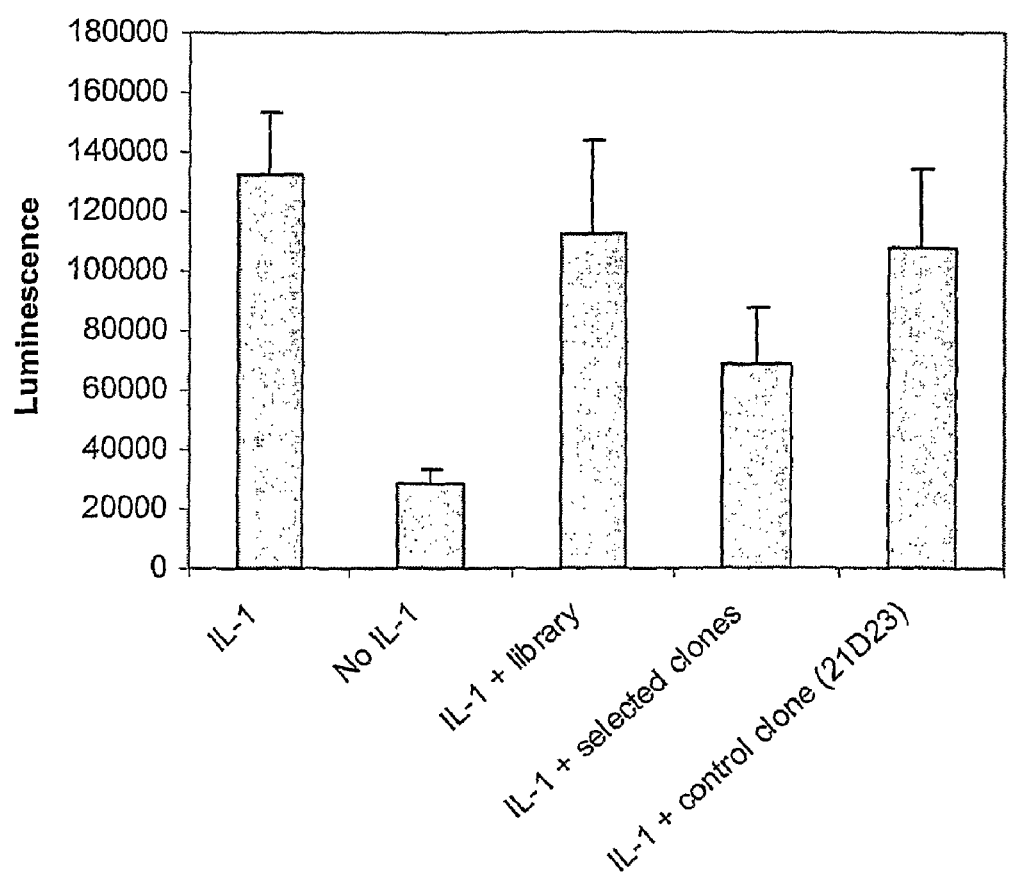
FIG. 1. In vitro inhibition of IL-1β induced activation of NFκB as determined using a reporter cell assay A FIND library, designated FIND3.1.2, containing the 13 mutations P38L, D47N, D47S, E52K, E52R, P53S, E75K, L78F, R92G, K93E, K93Q, K96M, V143I (relative to SEQ ID NO: 1), was generated, expressed and screened in the reporter assay as described below. From the 9856 clones screened, 400 clones were selected for secondary screening in the IL-6 assay.

Plates were further incubated in darkness for a further 5 minutes at 37° C. following the addition of 16 µl Steady Glo® Luciferase Assay system substrate (Promega). Luminescence was recorded using a FLUOstar OPTIMA obtained from BMG Labtech Results FIG. 1 shows the inhibition of IL-1β induced NF-κB activation (using the reporter cell assay) by mutant IL-1Ra polypeptides produced using the FIND® methodology. In a screen of the combined library (7392 clones) 400 top clones exhibiting the best inhibitory activity of IL-1β induced NF-κB activation (by about 50% compared to NF-κB activation induced by IL-1 alone) were identified and selected for further analysis.

FIG. 2 shows further results demonstrating the inhibition of IL-1β induced NF-κB activation (using the reporter cell assay) by mutant IL-1Ra polypeptides.

FIGS. 2(A), (B) and (C) show a significant reduction in the IC50 values for selected mutant IL-1Ra clones (all of which comprised an N-terminal 6× his tag), compared to the wild type IL-1Ra of SEQ ID NO:1.

FIG. 2(D) shows inhibition curves of mean luminescence of reporter cells against polypeptide concentration for the inhibition of IL-1β induced activation of NFκB by exemplary IL-1Ra mutant clones.

III. In Vitro Activity as Determined by Inhibition of IL-1β Induced IL-6 Production Introduction An alternative method for screening of the libraries of mutant IL-1Ra clones was based an assay that measures the capability of each mutant polypeptide to inhibit IL-1β induced IL-6 production. This cell-based assay was used to analyze the IL-1β inhibitory effect of the IL-1Ra mutants from culture supernatants of COS-7 cells transiently expressing the mutant polypeptides.

In additional experiments, the IL-1Ra mutants were expressed in and purified from *E. coli.*

Materials & Methods

MG-63 human osteocarcinoma cells, which express IL-1 receptors and produce IL-6 following stimulation with IL-1β, were cultured in 96-well micro-titer plates for 24 hours in the absence or presence of stepped doses of IL-1β (R&D) in D5 media (DMEM, Cambrex) supplemented with 5% (heat inactivated at 56° C. for 30 minutes) (Cambrex) at 37° C., 5% $CO_2$ to determine the minimum dose of IL-1β optimum IL-6 stimulation (0.3 ng/ml).

To determine the inhibitory factor of IL-1Ra mutants MG-63 cells were cultured for 24 hours in 96-well micro-titer plates in the presence or absence of stepped doses of mutant or wildtype IL-1Ra for 24 hours in D5 media (DMEM, Cambrex) supplemented with 5% (heat inactivated at 56° C. for 30 minutes) (Cambrex) at 37° C., 5% $CO_2$. The inhibitory activity of the mutants was determined by measuring the inhibition of IL-6 production in the cultures.

IL-6 production was determined by ELISA. In brief, Maxisorp 96-well plates (Nunc) were coated with 0.2 μg/well anti-human IL-6 antibody (R&D) in PBS overnight followed by blocking with 300 μl PBS 1% BSA per well for 1 hour and washed for 1 hour with (3×) 200 μl PBS 0.05% Tween-20 per well. Samples were diluted 40-fold in dilution buffer. Human IL-6 (R&D) was serial diluted in dilution buffer as a standard. 100 μl of diluted sample/standard was added in per well and incubated for 1 hour. Following washing 20 ng/well of biotinylated anti-human IL-6 antibody (R&D) diluted in dilution buffer was added and incubated for 1.5 hours. After washing for 30 minutes with (3×) 200 μl PBS 0.05% Tween-20, 100 μl/well of Steptavidin-HRP (R&D) diluted 200-fold in dilution buffer was added and incubated for 20 minutes.

After final washing, chromogenic detection was carried out using SIGMA-FAST™ o-phenylenediamine dihydrachloride tablets (SIGMA-Aldrich, St Louis, Mo., USA) according to the manufacturer's instructions. 2 M $H_2SO_4$ was added and the absorbance at 492 nm was measured in a SpectraMax plate reader using the Softmax pro software. All steps were performed at room temperature.

Results

FIG. 3 shows the IC50 values for inhibition of IL-1β induced IL-6 production by mutant IL-1Ra polypeptides produced using the FIND® methodology.

In FIG. 3(A), the exemplary clones tested all exhibited significantly lower IC50 values, compared to wild type IL-1Ra, for inhibition of IL-1β induced IL-6 production. The IC50 values for additional clones are shown in FIG. 3(B).

IV. In Vivo Efficacy of IL-1Ra Polypeptides of the Invention

Introduction

The in vivo activity of exemplary IL-1Ra polypeptides of the invention was determined by a capacity to retard the symptomatic development of collagen-induced arthritis (CIA) mice.

CIA is a widely accepted animal model for rheumatoid arthritis (RA). The RA-like disease is induced by immunization of mice or rats with collagen and disease severity is primarily determined as paw swelling. In addition, joint histology, cartilage and bone degradation and levels of cytokines in synovial fluid, serum or cultivated cells can be used to further examine disease severity. CIA can be used to investigate the ability of drug candidates to inhibit disease development and was used to compare the ability of an IL-1Ra mutant to inhibit CIA with that of wild type IL-1ra.

Materials and Methods

Male DBA-1 Janvier mice were intravenously injected at the base of the tail with 100 μl of complete Freunds adjuvant (Difco) supplemented with 1 μg/ul type II collagen and 3 μg/μl *Mycobacterium Tuberculosis* (Difco's H37RA, 231141) on day 0. On day 21, mice were boosted with an intraperitoneal injection of 100 ul of saline supplemented with 1 μg/ul type II collagen. Mice were scored macroscopically on each paw for arthritis development three times per week, according to the following system:

0 No visual inflammation
0.25 One inflamed toe
0.5 two or three inflamed toes
0.75 inflamed ankle or wrist
1.5 more than three toes and ankle or wrist moderately inflamed
2.0 severe inflamed toes and ankle or wrist A maximum score of eight could result for each animal. When mice reached a mean score of 2, animals received one of the following treatments:

(a) treatment with citrate buffer (Control);
(b) Anakinra (Kineret™; 20 mg/ml);
(c) wildtype IL-1Ra with N-terminal 6× his tag (1, 5, or 20 mg/ml); or
(d) polypeptide of the invention with N-terminal 6× his tag (1, 5, or 20 mg/ml).

Clone '23B2' was used as an exemplary polypeptide of the invention, which comprises the amino acid sequence of SEQ ID NO: 1 with substitutions P38L, E52K, E75K, K93Q and V143I. Clone '23B2' also comprises an N-terminal 6× his tag.

Mini-osmotic pumps type 1007D (Alzet, Cupertino, Calif., USA) were loaded with citrate buffer (5 mM citric acid, 90 mM NaCl, 0.35 mM EDTA, 0.07% Tween 80), 20 mg/ml Anakinra (Kineret™) or his-tagged wildtype IL-1Ra or his-tagged polypeptide of the invention (dissolved in citrate buffer to a final concentration of 20, 5 or 1 mg/ml) and implanted intraperitoneally. A release rate of 0.5 μl/h from the pumps resulted in an Anakinra (Kineret™) dose of 240 μg/day and doses of 240, 60 and 12 μg/day of the wildtype IL-1Ra and polypeptide of the invention. Mice were scored macroscopically on each paw for arthritis development at days 0, 1, 4, 6 and 7 post implantation of the pump.

Following 7 days of treatment, the experiment was terminated and disease development from the start of the treatment until termination of the experiment determined as a macroscopic score.

Results

The effects of the treatment regimes on mean arthritic score in CIA mice is shown in FIG. 4.

An inhibition of arthritis development was observed with Anakinra (Kineret™) and with all doses of wildtype IL-1Ra and the exemplary polypeptide of the invention. However, the maximal inhibition of arthritis development was only observed with the highest dose (20 mg/kg) of Anakinra (Kineret™) and wildtype IL-1Ra. In contrast, the exemplary polypeptide of the invention was able to produce an identical level of inhibition at a lower dose of 5 mg/kg.

The invention claimed is:

1. An isolated interleukin-1 receptor antagonist (IL-Ra) polypeptide wherein the polypeptide comprises the amino acid sequence selected from the group consisting of:
  (a) SEQ ID NO: 1 with mutations P38L, D47N, E52R, E75K, R92G, K96M and V143I;
  (b) SEQ ID NO: 1 with mutations P38L, D47N, E52R, E75K and K93E;
  (c) SEQ ID NO: 1 with mutations D47N, E52R, L78F and K93E;
  (d) SEQ ID NO: 1 with mutations E52R and K93Q;
  (e) SEQ ID NO: 1 with mutations P38Y, D47N, E52R, E90Y and M136N;
  (f) SEQ ID NO: 1 with mutations P38Y, D47N, E52R, H54R, E90Y and M136N;
  (g) SEQ ID NO: 1 with mutations D47N, E52R, H54R and E90Y;
  (h) SEQ ID NO: 1 with mutations D47N, E52R, H54R, E90Y, Q129L and M136N; and
  (i) SEQ ID NO: 1 with mutations P38L, E52K, E75K, K93Q and V143I
  j) SEQ ID NO: 1 with mutations P38L, D47N, E52K and K93E;
  (k) SEQ ID NO: 1 with mutations D47N, E52K, E75K and K93Q;
  (l) SEQ ID NO: 1 with mutations P38L and E52K;
  (m) SEQ ID NO: 1 with mutations E52R;
  (n) SEQ ID NO: 1 with mutations E52K;
  (o) SEQ ID NO: 1 with mutations E52K and T109I;
  (p) SEQ ID NO: 1 with mutations E52K and P107T;
  (q) SEQ ID NO: 1 with mutations P38L, D47N, E52R, L78F and K93E;
  (r) SEQ ID NO: 1 with mutations P38L, D47N, E52K, R92G and K93E;
  (s) SEQ ID NO: 1 with mutations D47N, E52K, H54R, E75K, K93Q;
  (t) SEQ ID NO: 1 with mutations D47S, E52K, P53S, E75K and K93Q;
  (u) SEQ ID NO: 1 with mutations P38L, E52K, E75K and K93Q;
  (v) SEQ ID NO: 1 with mutations P38L, E52K, E75K, K93Q and Q129L;
  (w) SEQ ID NO: 1 with mutations P38L, E52K, E75K, Q79L and K93Q;
  (x) SEQ ID NO: 1 with mutations P38L, E52K, E75K, E90G, K93E and D104Y;
  (y) SEQ ID NO: 1 with mutations P38L, E52K, K93E and K96M;
  (z) SEQ ID NO: 1 with mutations P38L, E52K, A82T, K93E and S110R;
  (aa) SEQ ID NO: 1 with mutations P38L, D47N, E52K, E75K, K93Q and D138G;
  (bb) SEQ ID NO: 1 with mutations P38L, K45Q, D47N, E52K, E75K, K93Q and V143I;
  (cc) SEQ ID NO: 1 with mutations E52K and K93E;
  (dd) SEQ ID NO: 1 with mutations P38L, E52K, E75K and K93Q;
  (ee) SEQ ID NO: 1 with mutations P38Y, E52R and E90Y;
  (ff) SEQ ID NO: 1 with mutations P38Y, E52R, E90Y and M136N;
  (gg) SEQ ID NO: 1 with mutations P38Y, E52R, H54R, E90Y and M136N;
  (hh) SEQ ID NO: 1 with mutations P38Y, D47N, E52R, E90Y, Q129L and M136N;
  (ii) SEQ ID NO: 1 with mutations E52R, E90Y and M136N;
  (jj) SEQ ID NO: 1 with mutations P38L, L42F, E52K, E75K, K93Q and M136K
  (kk) SEQ ID NO: 1 with mutations D47N, E52K, E75K, K93Q and K145E;
  (ll) SEQ ID NO: 1 with mutations P38L, E52K and N84S;
  (mm) SEQ ID NO: 1 with mutations P38L, E52K and K93E;
  (nn) SEQ ID NO: 1 with mutations P38L, D47N, E52R, L78F, K93E and V143I;
  (oo) SEQ ID NO: 1 with mutations P38L, D47N, E52R, R92G, K96M and V143I;
  (pp) SEQ ID NO: 1 with mutations P38L, D47N, E52R, R92G and K96M;
  (qq) SEQ ID NO: 1 with mutations P38L, L78F and K93E;
  (rr) SEQ ID NO: 1 with mutations P38L, D47N, E52R, E75K, L78F and K93E;
  (ss) SEQ ID NO: 1 with mutations P38L, D47N, E52R, E75K and K93Q;
  (tt) SEQ ID NO: 1 with mutations P38L, E52K, R92G and K96M;
  (uu) SEQ ID NO: 1 with mutations P38L, E52K, E75K and K93Q;
  (vv) SEQ ID NO: 1 with mutations P38L, D47S, E52K, P53S, E75K, R92G and K96M;
  (ww) SEQ ID NO: 1 with mutations P38L, R92G and K96M;

(xx) SEQ ID NO: 1 with mutations D47N, E52R, R92G and K96M;
(yy) SEQ ID NO: 1 with mutations E52R, L78F, N84D and K93E;
(zz) SEQ ID NO: 1 with mutations E52R, E75K, R92G, K96M and V143I;
(aaa) SEQ ID NO: 1 with mutations L78F, A82V, R92G and K96M;
(bbb) SEQ ID NO: 1 with mutations D47S, E52K, P53S, E75K, R92G and K96M;
(ccc) SEQ ID NO: 1 with mutations D47S, E52K, P53S, R92G and K96M;
(ddd) SEQ ID NO: 1 with mutations E75K, R92G, K96M and V143I;
(eee) SEQ ID NO: 1 with mutations E75K and K93Q;
(fff) SEQ ID NO: 1 with mutations E75K, E90G, K93Q and V143I;
(ggg) SEQ ID NO: 1 with mutations E75K and K93E;
(hhh) SEQ ID NO: 1 with mutations R92G, K96M and V143I;
(iii) SEQ ID NO: 1 with mutations R92G and K96M;
(jjj) SEQ ID NO: 1 with mutations P38Y and E52R;
(kkk) SEQ ID NO: 1 with mutations P38Y, E52R and M136N;
(lll) SEQ ID NO: 1 with mutations P38Y, E90Y and M136N;
(mmm) SEQ ID NO: 1 with mutations P38Y, D47N, E52R and Q129L;
(nnn) SEQ ID NO: 1 with mutations P38Y, H54R, E90Y and Q129L;
(ooo) SEQ ID NO: 1 with mutations P38Y, P53S, Q129L and M136N;
(ppp) SEQ ID NO: 1 with mutations P38Y, D47N, E52R and M136N;
(qqq) SEQ ID NO: 1 with mutations P38Y, E52R, H54R and E90Y;
(rrr) SEQ ID NO: 1 with mutations P38Y, E52R, P53S, Q129L and M136N;
(sss) SEQ ID NO: 1 with mutations P38Y, P53S, H54R, E90Y and Q129L;
(ttt) SEQ ID NO: 1 with mutations P38Y, P53S, E90Y, Q129L and M136N;
(uuu) SEQ ID NO: 1 with mutations P38Y, D47N, P53S, E90Y and Q129L;
(vvv) SEQ ID NO: 1 with mutations P38Y, D47N, E52R, Q129L and M136N;
(www) SEQ ID NO: 1 with mutations P38Y, D47N, H54R, E90Y, Q129L and M136N;
(xxx) SEQ ID NO: 1 with mutations P38Q, E52R and E90Y;
(yyy) SEQ ID NO: 1 with mutations D47N, E90Y, Q129L and M136N;
(zzz) SEQ ID NO: 1 with mutations D47N, P53S, H54R, Q129L and M136N;
(aaaa) SEQ ID NO: 1 with mutations D47N, E52R, P53T, H54R, E90Y, Q129L and M136N:
(bbbb) SEQ ID NO: 1 with mutations E52R and E90Y;
(cccc) SEQ ID NO: 1 with mutations E52R and H54R;
(dddd) SEQ ID NO: 1 with mutations E52R, H54R, E90Y and M136N;
(eeee) SEQ ID NO: 1 with mutations E52R, H54R, E90Y, Q129L and M136N;
(ffff) SEQ ID NO: 1 with mutations P53S, H54R, E90Y, Q129L and M136N; and
(gggg) SEQ ID NO: 1 with mutations E90Y Q129L and M136N.

2. A pharmaceutical formulation comprising the polypeptide
according to claim 1 in admixture with a pharmaceutically or veterinarily acceptable adjuvant, diluent or carrier.

3. A pharmaceutical formulation according to claim 2 suitable for parenteral administration to a human.

4. The isolated polypeptide of claim 1, wherein the polypeptide further comprises a human IgG Fc region or human serum albumin.

5. The isolated polypeptide of claim 1, wherein the polypeptide exhibits an enhanced biological activity compared to wild type IL-1Ra; wherein the enhanced biological activity is
(a) increased binding affinity for IL-1 receptors, or
(b) increased binding kinetics.

6. The isolated polypeptide of claim 4, wherein the polypeptide exhibits an enhanced biological activity compared to wild type IL-1Ra; wherein the enhanced biological activity is increased half-life in vivo.

7. The isolated polypeptide of claim 1, wherein the polypeptide is capable of inhibiting IL-1β-induced NFκB activation in an in vitro reporter assay and/or inhibiting IL-1β-induced production of IL-6 in vitro.

* * * * *

SEQUENCE LISTING

```
<160> NUMBER OF SEQ ID NOS: 2

<210> SEQ ID NO 1
<211> LENGTH: 152
<212> TYPE: PRT
<213> ORGANISM: Homo sapiens

<400> SEQUENCE: 1

Arg Pro Ser Gly Arg Lys Ser Ser Lys Met Gln Ala Phe Arg Ile Trp
1               5                   10                  15

Asp Val Asn Gln Lys Thr Phe Tyr Leu Arg Asn Asn Gln Leu Val Ala
            20                  25                  30

Gly Tyr Leu Gln Gly Pro Asn Val Asn Leu Glu Glu Lys Ile Asp Val
        35                  40                  45

Val Pro Ile Glu Pro His Ala Leu Phe Leu Gly Ile His Gly Gly Lys
    50                  55                  60

Met Cys Leu Ser Cys Val Lys Ser Gly Asp Glu Thr Arg Leu Gln Leu
65                  70                  75                  80

Glu Ala Val Asn Ile Thr Asp Leu Ser Glu Asn Arg Lys Gln Asp Lys
                85                  90                  95

Arg Phe Ala Phe Ile Arg Ser Asp Ser Gly Pro Thr Thr Ser Phe Glu
            100                 105                 110

Ser Ala Ala Cys Pro Gly Trp Phe Leu Cys Thr Ala Met Glu Ala Asp
        115                 120                 125

Gln Pro Val Ser Leu Thr Asn Met Pro Asp Glu Gly Val Met Val Thr
    130                 135                 140

Lys Phe Tyr Phe Gln Glu Asp Glu
145                 150

<210> SEQ ID NO 2
<211> LENGTH: 177
<212> TYPE: PRT
<213> ORGANISM: Homo sapiens

<400> SEQUENCE: 2

Met Glu Ile Cys Arg Gly Leu Arg Ser His Leu Ile Thr Leu Leu Leu
1               5                   10                  15

Phe Leu Phe His Ser Glu Thr Ile Cys Arg Pro Ser Gly Arg Lys Ser
            20                  25                  30

Ser Lys Met Gln Ala Phe Arg Ile Trp Asp Val Asn Gln Lys Thr Phe
        35                  40                  45

Tyr Leu Arg Asn Asn Gln Leu Val Ala Gly Tyr Leu Gln Gly Pro Asn
    50                  55                  60

Val Asn Leu Glu Glu Lys Ile Asp Val Val Pro Ile Glu Pro His Ala
```

```
65                  70                  75                  80
Leu Phe Leu Gly Ile His Gly Lys Met Cys Leu Ser Cys Val Lys
                85                  90                  95

Ser Gly Asp Glu Thr Arg Leu Gln Leu Glu Ala Val Asn Ile Thr Asp
            100                 105                 110

Leu Ser Glu Asn Arg Lys Gln Asp Lys Arg Phe Ala Phe Ile Arg Ser
        115                 120                 125

Asp Ser Gly Pro Thr Thr Ser Phe Glu Ser Ala Ala Cys Pro Gly Trp
    130                 135                 140

Phe Leu Cys Thr Ala Met Glu Ala Asp Gln Pro Val Ser Leu Thr Asn
145                 150                 155                 160

Met Pro Asp Glu Gly Val Met Val Thr Lys Phe Tyr Phe Gln Glu Asp
                165                 170                 175

Glu
```